(12) United States Patent
Blomeyer

(10) Patent No.: US 8,319,134 B2
(45) Date of Patent: Nov. 27, 2012

(54) ELECTROSURGICAL PENCIL SWITCH, CIRCUITRY, AND METHOD OF ASSEMBLY

(75) Inventor: Michael Blomeyer, Walnut Creek, CA (US)

(73) Assignee: E Surgical, LLC, Walnut Creek, CA (US)

( * ) Notice: Subject to any disclaimer, the term of this patent is extended or adjusted under 35 U.S.C. 154(b) by 0 days.

(21) Appl. No.: 13/136,303

(22) Filed: Jul. 28, 2011

(65) Prior Publication Data
US 2011/0319892 A1 Dec. 29, 2011

Related U.S. Application Data

(63) Continuation-in-part of application No. 12/456,622, filed on Jun. 19, 2009, now Pat. No. 8,022,327.

(51) Int. Cl.
| | |
|---|---|
| H01H 1/06 | (2006.01) |
| H01H 11/00 | (2006.01) |
| H01H 13/04 | (2006.01) |
| A61B 18/14 | (2006.01) |

(52) U.S. Cl. ....... 200/505; 200/284; 200/292; 200/52 R; 200/275; 606/42; 606/45; 606/49; 29/844; 29/848; 29/854

(58) Field of Classification Search ............. 200/512, 200/275, 505, 284, 52 R, 292; 600/45, 42, 600/49; 29/622, 844, 848, 854
See application file for complete search history.

(56) References Cited

U.S. PATENT DOCUMENTS

| | | | | |
|---|---|---|---|---|
| 3,801,766 | A * | 4/1974 | Morrison, Jr. | 200/553 |
| 4,032,738 | A * | 6/1977 | Esty et al. | 606/42 |
| 4,443,935 | A * | 4/1984 | Zamba et al. | 29/622 |
| 4,492,832 | A * | 1/1985 | Taylor | 200/52 R |
| 4,545,375 | A * | 10/1985 | Cline | 606/42 |
| 4,619,258 | A * | 10/1986 | Pool | 606/42 |
| 4,625,723 | A * | 12/1986 | Altnether et al. | 606/42 |
| 4,655,215 | A * | 4/1987 | Pike | 606/42 |
| 5,015,227 | A * | 5/1991 | Broadwin et al. | 604/22 |
| 5,226,904 | A * | 7/1993 | Gentelia et al. | 606/42 |
| 5,376,089 | A * | 12/1994 | Smith | 606/42 |
| 5,541,376 | A * | 7/1996 | Ladtkow et al. | 200/284 |
| 5,817,091 | A * | 10/1998 | Nardella et al. | 606/38 |
| 5,817,093 | A * | 10/1998 | Williamson et al. | 606/50 |
| 6,500,169 | B1 * | 12/2002 | Deng | 606/1 |
| 7,173,206 | B2 * | 2/2007 | Du Pont | 200/406 |

FOREIGN PATENT DOCUMENTS

GB 2094555 A * 9/1982

* cited by examiner

*Primary Examiner* — Briggitte R Hammond
(74) *Attorney, Agent, or Firm* — Thomas W. Cook

(57) ABSTRACT

Formation of an assemblage of electrically conductive components for a new electrosurgical pencil is disclosed, and assembly of those components in a method for automating the manufacture and combination of current carrying metal circuitry and operable switching components in "electrosurgical pencils" which supply current to an active terminal, for application of high frequency or high power electrical current to a surgical site, and control of such current through coaction of the elements of the switch. In manufacture, the design of the switch components allows start-to-finish automated assembly of the switch, whereby an array of identical multiple metal "frames" may be formed from a reel, then each frame separated and enclosed within molded plastic, and the resulting cabinet joined with a housing to create an inexpensive hand piece, for use with a high quality, reusable cable and plug assembly.

5 Claims, 21 Drawing Sheets

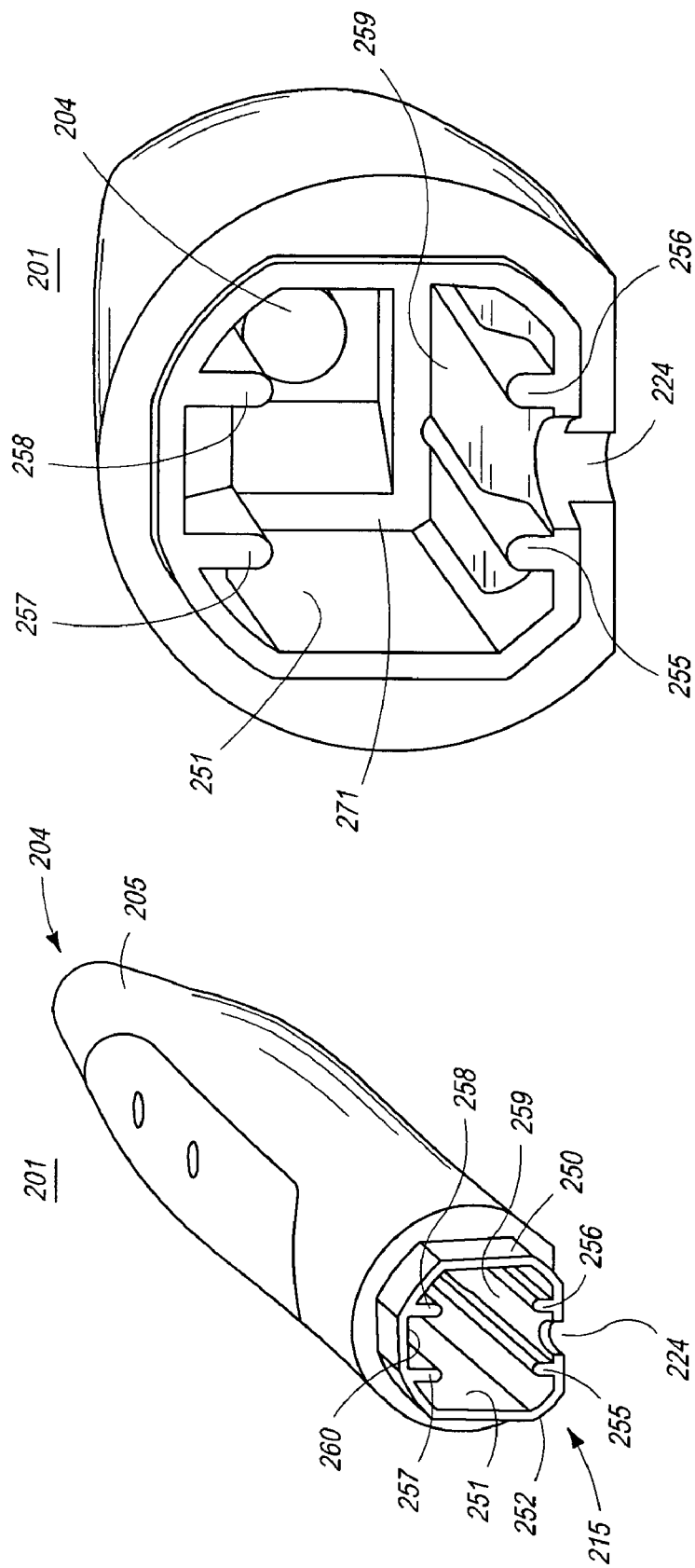

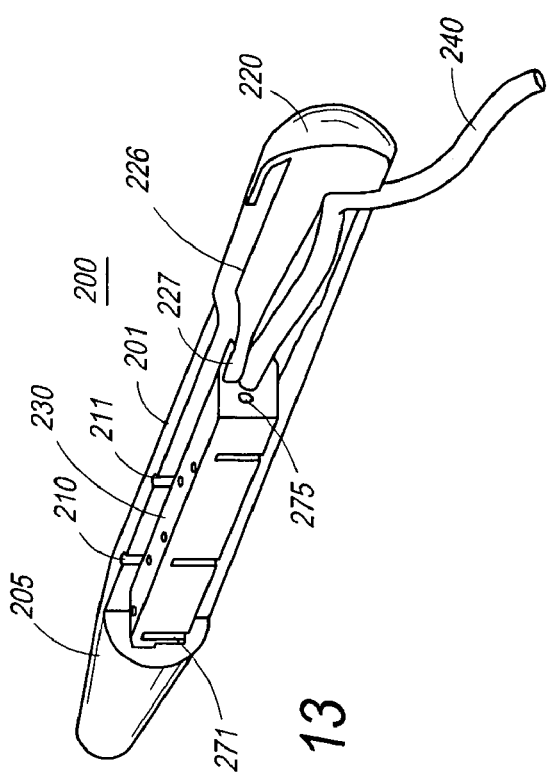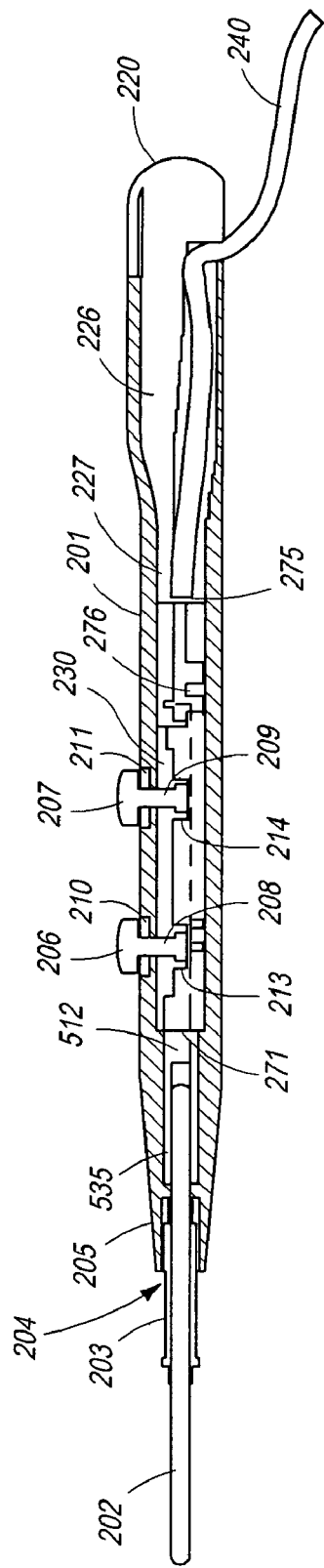

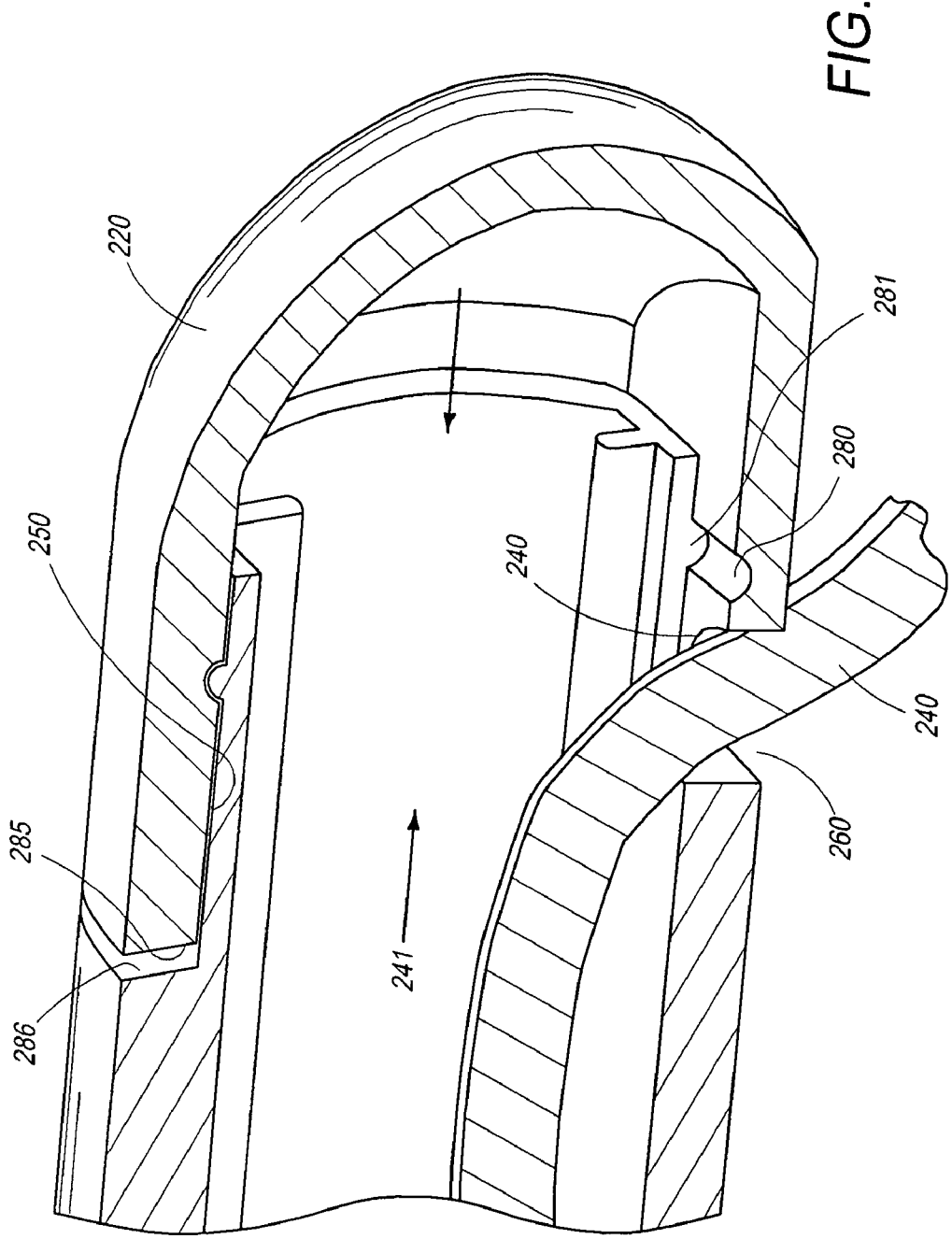

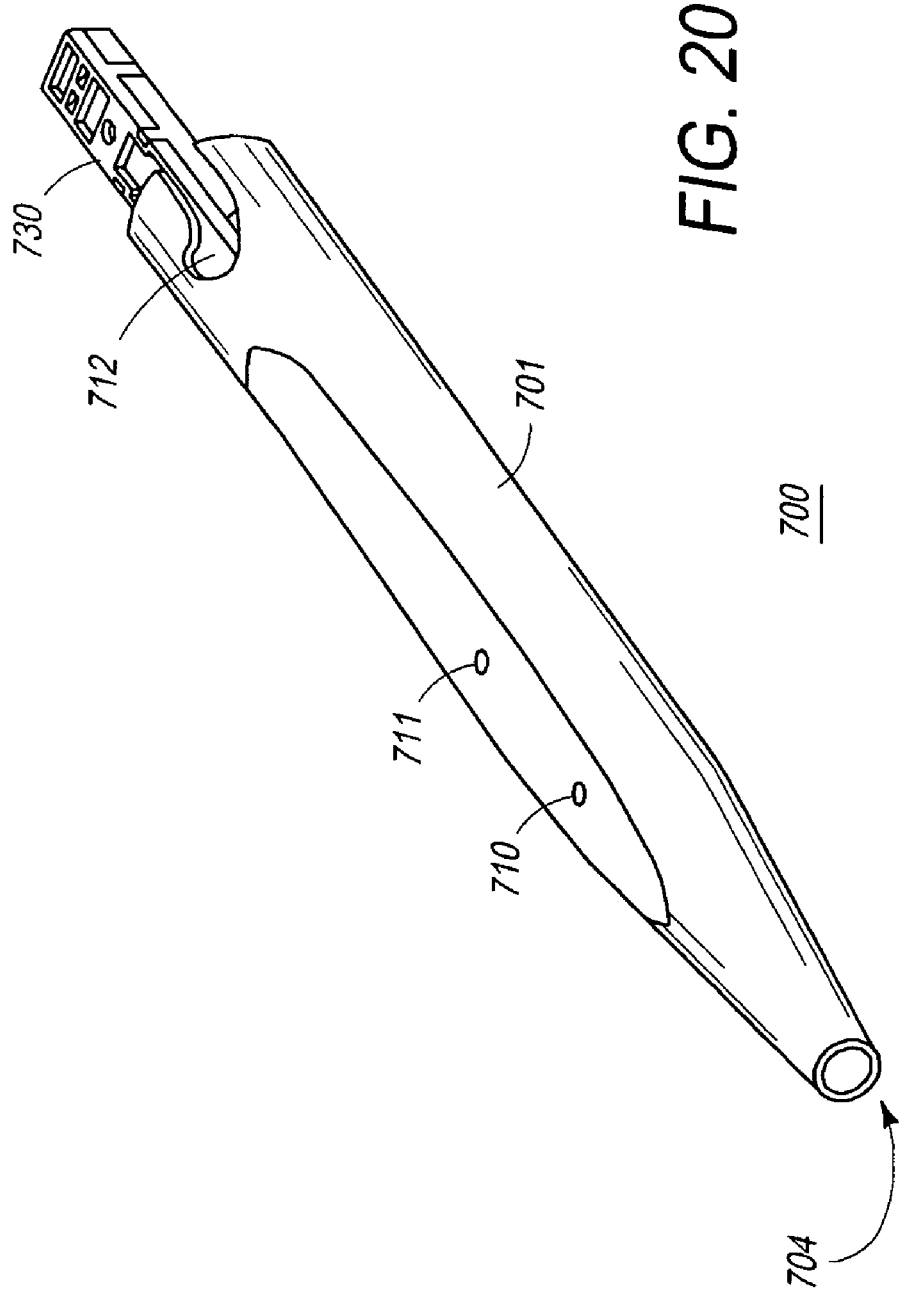

ELECTROSURGICAL PENCIL SWITCH, CIRCUITRY, AND METHOD OF ASSEMBLY

CROSS REFERENCE TO RELATED APPLICATIONS

This application is a continuation-in-part of application Ser. No. 12-456,622, filed Jun. 19, 2009, now U.S. Pat. No. 8,022,327, from which applicant claims priority.

TECHNICAL FIELD OF THE INVENTION

The present invention relates to an assemblage of electrically conductive components for power switching in electrical apparatus hand pieces, and to automated assembly of the such components into a molded insulative holding and positioning body (herein the "Cabinet"). More specifically, the present invention is a method for automating the manufacture and combination of current carrying metal circuitry, and associated switching components, which allows further automated assembly of such circuitry, switching components, and a Cabinet into the hollow body housing of an electrosurgical apparatus. The assembly of the present invention creates an improved tool for surgical cutting, coagulation, and cauterizing. Such tools are generally referred to in surgery as "electrosurgical pencils" ("EP"), and the present invention, when placed in such a housing, will generally be termed herein the "hand piece" of the "Pencil." When the Cabinet and the electrically conductive components are eventually assembled into the hand piece of the Pencil, the present invention specifically includes the electrically coacting apparatus of the circuitry activation components, along with the Cabinet, which altogether comprise the operable conductive and non-conductive components for opening and closing the circuit. The combination of electrically conductive components into circuitry within the Cabinet, ready to be inserted into the hand piece of the Pencil, will generally be termed herein the "Switch." The Switch supplies and controls current to an active terminal at the distal end of the Pencil. In operation, the Pencil allows, at its distal end, the application of high frequency or high power electrical current to a surgical site, and control of such current through coaction of the elements of the Switch.

In the manufacturing process associated with the Switch and Cabinet, as disclosed herein, the design of the Switch components within the Cabinet allows start-to-finish automated assembly of the Switch and the Pencil, in an industry which knows only partially automated assembly, and partial assembly by hand. This is accomplished by a large-scale manufacture, in which an array of identical multiple metal "frames" may be formed from a larger metal blank, or from a "reel" of metal, then each metal frame may be separated from each other metal frame, either before or after the metal frames are enclosed within a corresponding number of the molded plastic components of the Cabinets.

The present invention also relates to electrosurgical Pencils, utilizing a low cost version of the Switch and Cabinet of the present invention, along with exterior Pencil hand piece "Housing" members, and high quality electrical conductors designed to carry the current necessary to operate the Pencil from an electrical generator to the Pencil. Such Housing members and conductors are formed to be easily and securely attached and separated from the hand piece of the Pencil. The design of the Switch, Cabinet, and Housing components allows start-to-finish automated assembly of the hand piece of the Pencil. The design of the electrical conductors by which the Pencil is electrically connected to the generator, similarly allows automated assembly of the conductors, and reusability of the conductors. Automated assembly of the hand piece and conductors together allows fully automated assembly of an entire electrosurgical pencil unit. Cost savings are thereby achieved in an industry which knows only partially automated assembly, and partial assembly by hand.

Automated assembly of the hand piece of the Pencil in turn allows dramatic reduction in costs to manufacture the hand piece of the Pencil. As a result, the Pencil hand piece may be connected to the electrical generator using the quality electrical conductors of the present invention, the inexpensive Pencil hand piece may be discarded as surgical waste after only a single use, and the more costly electrical conductors reused many times with replacement Pencil hand pieces, at significant additional cost savings, while reducing medical waste dramatically.

BACKGROUND ART OF THE INVENTION

Electrosurgical instruments have become widely used by surgeons in recent years. Most electrosurgical instruments include a. hand-held instrument, or pencil, which transfers radio-frequency (RF) electrical energy (electrical current) to a tissue site. The electrical current may be returned to the source via a return electrode pad positioned under a patient (typically monopolar use), or a smaller return electrode positioned in bodily contact, with or immediately adjacent to, the surgical site (typically bipolar use). The waveforms which result from the RF electrical current may be used to produce a variety of effects, depending on the power applied, and the frequency used. These effects include surgical cutting, coagulation, and cauterizing (or sealing), by application of electric current to biological tissue. The current is produced by radio-frequency electrical energy generated from an appropriate electrosurgical generator.

These useful effects are produced during surgery by "electrosurgical pencils" ("EP") surgical instruments which have a hand piece, to which is attached an active electrode at one end, and a generator at the other end. The main body of the hand piece for most electrosurgical pencils is comprised of a molded plastic hand piece, within which resides a second plastic holder, for positioning and holding appropriate electrical circuitry, which acts as a conduit for electrical current, and a switch (or switches) by which the current may be controlled. The active electrode, at the distal end of the electrosurgical pencil, is, by such switch or switches, electrically connected, through the electrical circuitry within the interior plastic holder, to a suitable RF source of electrical current (i.e., an electrosurgical generator, or "generator") which produces the radio-frequency electrical energy necessary for the operation of the electrosurgical pencil.

In general, when a surgical procedure is performed on a patient using a monopolar electrosurgical pencil, electrical energy from the generator is conducted through the active electrode to the tissue at the site of the operation or incision, and then through the patient to a return electrode. The return electrode is typically placed at a convenient place on the patient's body and is attached to the generator by a conductive material. The active electrode is an electrically conducting element which comes in a variety of forms and shapes, so that the surgeon may apply the electrical energy from the electrosurgical pencil to the patient in a variety of ways.

When a surgical procedure is performed on a patient using a bipolar electrosurgical pencil, electrical energy from the generator is conducted through and active electrode to the tissue at the site of the operation, and then through the patient tissue to a return electrode. The return electrode in such case is proximal to the active electrode, typically within millimeters distance, and provides a return path to the generator, alleviating the need for a separate return pad electrode as used in monopolar procedures.

The electrosurgical pencils already in use may be operated by a hand switch or a foot switch. However, hand switching on the hand piece of the electrosurgical pencil has become the standard method for changing the electrical current from that suitable for surgical cutting, to coagulation and cauterizing, and back to cutting. Typically, electrosurgical instrument systems allow the surgeon to change between two pre-configured settings (i.e., coagulation and cutting) via two discrete buttons disposed on the exterior of the electrosurgical pencil (external "Buttons"). Such Buttons, when pressed, generally activate another conductive or non-conductive component, which then activates the conductive switching elements of the electrosurgical pencil, thereby allowing current to flow through the electrosurgical pencil to the active electrode. Other switching arrangements have been developed, including three-button systems and rocker-arm systems, depending on the number of functions which are desired, and the surgeon's preferred switching "feel" and activation method.

Regardless of the switch type and number of settings, many switches for electrosurgical pencils presently in use utilize suitably sized and stamped metal to form the electrical circuitry which carries current from the electrical generator leads, through one or more electrical conductors (or conducting strips), to the active electrode. Other switches for electrosurgical pencils include the use of small printed circuit boards ("PCBs"), with various attached connectors. Once a switch has been assembled, typically by hand, at least in part using present technology and methods, it may then be incorporated as a sub-assembly into the hand piece of an electrosurgical pencil, and the pencil assembly completed (again by hand at least in part).

Examples of such stamped electrical circuitry may be found in U.S. Pat. Nos. 5,376,089 and 4,427,006. U.S. Pat. No. 5,376,089 shows an invention in which the circuitry of the electrosurgical pencil switch is stamped in a single piece, to form the totality of the switching circuitry, and then stamped again at a number of "punch points," to electrically isolate each of the conducting strips of the switch after the conducting strips are positioned and secured within a housing. After securing the conducting strips, the switch sub-assembly is then assembled within the housing of an electrosurgical pencil.

One benefit of stamping switch circuitry in a single piece is ease of manufacture, as stamping all the circuitry in a single piece avoids wiring by hand in a "bread board" fashion, with conducting wire and solder. Another benefit of stamping switch circuitry is the creation, with one single stamping, of numerous electrical conducting strips necessary to conduct current from generator leads to active electrode. At the same time, the stamping operation may be used to create electrical spring contacts, as in U.S. Pat. No. 5,376,089, or "cantilevered conductor strips," as in U.S. Pat. No. 4,427,006 (these contacts, may generally be termed "Spring Contacts," and the contacts disclosed herein of this type "Activation Straps"). Spring Contacts generally provide the resistive mechanism necessary to make or break electrical contact between the generator leads and the active electrode. In operation, Spring Contacts may flex, to make electrical contact between the otherwise electrically isolated electrical strips of the electrosurgical pencil switch circuitry. Flexing of the Spring Contacts occurs when buttons which may be reached and activated from the exterior of the electrosurgical pencil hand piece are pressed. As resilient pieces, however, the Spring Contacts may also return to their original positions, or move partially to their original positions, to break electrical contact, and thereby again electrically isolate the electrical strips of the electrosurgical pencil switch circuitry. This occurs when pressure on the accessible exterior buttons is reduced.

The largest single problem with most common switching arrangements is that, while the electrosurgical pencil switch circuitry of a single switch may be stamped in a single piece, the conducting strips of the circuitry must be stamped again at the "punch points" to electrically isolate each of the conducting strips. This second, punch point, stamping currently takes place before the conducting strips of the electrosurgical pencil switch circuitry are fastened in place within the molded insulative holding and positioning body of the hand piece of the electrosurgical pencil. As a result, the conducting strips of the electrosurgical pencil switch circuitry, or other necessary electrical components such as "dome switches," must be located by human eyes, selected with human thought, and touched by human hands. Hand labor, in fact, is often necessary, depending on the arrangement utilized, to locate the correct electrical component for loading into the molded insulative holding and positioning body, positioning such components within that body, or fastening such components in place. As the electrical components of electrosurgical pencil switches are small, such work by humans is slow, sometimes inaccurate, and often requires special tools or fasteners. Moreover, because switches are currently manufactured on assembly lines, such lines are formed to accommodate a stream of single switches, rather than allowing assembly of components when electrical conductors are "ganged," or otherwise joined. That is, under current practice, electrical conductors for switches are generally formed, by stamping, one at a time. Where electrical conductor stamping for multiple switches does take place, the form of the electrical conductors, and the form of the non-electrical components, does not allow the assembly of switches as a group, or even as an attached line of switches or switch components. Instead, electrical conductors intended for individual switches are separated one from another before switch assembly under all assembly methods currently in place. As a result, the handling by human eyes, thought, and hands, and the consequent slowness and inaccuracies is magnified, thereby increasing costs.

In a small number of switching arrangements where the circuitry is stamped in a single piece; the conducting strips of the circuitry may be stamped at the punch points to electrically isolate each of the conducting strips after the conducting strips are fastened in place within the molded insulative holding body of the hand piece. This kind of manufacture, which may be seen in U.S. Pat. No. 5,376,089, allows the elimination of some human handling of small switch parts. However, using this patent as but one example, some assembly by hand is still necessary even in the invention of this patent, as the dome shaped members which make contact with underlying Spring Contacts must be positioned after the molded insulative holding body of the hand piece is assembled, and sealing tape is placed over such dome shaped members. As a result, some conductive (and non-conductive) components of this electrosurgical pencil switch, and indeed all present switches, presently must still be located, selected, and positioned by human hands.

Another large problem with all present electrosurgical pencils is that the entire assembly, from the active electrode all the way back to the electrical generator leads, and including the hand piece, with its switch and housing members, and also the electrical conductors by which the pencil is electrically connected to the generator, is discarded as medical waste.

As electrosurgical pencils are, even when assembled by humans, relatively small and simple devices, and used by medical professionals under circumstances which may benefit from a "disposable" tool, electrosurgical pencils have become less expensive to produce. However, like most manufactured items, and all medical tools (especially inexpensive medical tools), the cost of manufacture, and the distribution of electrosurgical pencils, along with the necessity to repurchase such "disposable" tools as they are discarded, adds greatly to their overall cost to the surgical profession and, ultimately, to their patients and health care costs. What is needed, then, is an even less resource intensive method of manufacturing electrosurgical pencils. The savings in resources may be achieved at the stage where the electrosurgical pencil switch circuitry is loaded into the molded insulative holding and positioning body of the electrosurgical pencil hand piece. Further savings may be achieved if a very low cost hand piece, which may be discarded after use, is matched with high quality electrical conductors (leading from the hand piece back to the generator), which may be retained and reused.

The Switch of the Pencil of the present invention reduces the cost of manufacture of electrosurgical pencil by eliminating human selection and handling during the assembly of electrosurgical pencil switches and hand pieces. The design of the Switch allows this through an innovative design in the Switch circuitry and other electrical components, which allows 100% machine assembly (i.e., the assembly of the Switch and Cabinet of the hand piece is entirely automated), and by use of otherwise common components. The present invention thereby overcomes the cost drawbacks of prior devices, saving significant manufacturing costs, which results in the saving of dollars of unnecessary cost to the surgeon, and tens of dollars of extra cost to the patient or her insurer. The Pencil of the present invention is also formed so that this low resource using Switch is formed so that it may be joined with high quality electrical conductors leading back to the generator. Accordingly, huge savings in cost of production and distribution may be achieved when, as a surgical procedure comes to a conclusion, the inexpensive hand piece is discarded as medical waste, but the expensive electrical generator conductors are saved, sterilized, and used many times again.

No patent or electrosurgical pencil of which the inventor is aware allows automation of the assembly of the electrosurgical pencil hand piece, to reduce costs, and free up direct human attention and effort. No electrosurgical pencil of which the inventor is aware allows the surgeon to finely select the tactile feel of her electrosurgical pencil by selecting activation button pressure and action in a electrosurgical pencil costing so little. And no electrosurgical pencil of which the inventor is aware allows production and distribution cost savings, and "recycling" of the most expensive part of the pencil, the electrical generator conductors, so that these components may be used many times again.

DISCLOSURE OF INVENTION

Summary of the Invention

In its simplest form, the Switch of the present invention is comprised in part of a first unitary, stamped, metal frame (the "First Frame"), formed to be molded integrally within a first non-conductive, top plastic (the First Frame and the top plastic together being the Switch "Top"), and a second unitary, stamped, metal frame (the "Second Frame"), formed to be molded integrally within a second non-conductive, bottom plastic (the Second Frame and the bottom plastic together being the Switch "Bottom"). During manufacture, the Top and the Bottom, each carrying its electrically conductive First Frame and Second Frame, are assembled one to the other, along with suitable conductors for connecting to a generator, and the Cabinet, with appended conductors, is inserted into an insulated surgical pencil "Housing."

In another embodiment of the present invention, the First Frame, formed and molded into a Top as before, and the Second Frame, formed and molded into a Bottom as before, are assembled one to the other during manufacture without the conductors for connecting to a generator, and then the Cabinet is inserted into the insulated surgical pencil Housing. In this version of the present invention, the Housing is closed by an assembly of suitable conductors, formed into the closing cap in such a fashion as to allow pins within the closing cap to connect electrically with corresponding leads emanating from the Cabinet. The Cabinet leads are ends of the First Frame and Second frame protruding from the Cabinet, and formed to easily make contact with the corresponding pins of the closing cap.

Spring Contacts in the form of Activation Straps, formed in the First Frame or the Second Frame may be reached in all versions of the Switch of the present invention. The Activation Straps may be activated by a surgeon from the exterior of the electrosurgical pencil housing with buttons (the "Buttons"), which have stems which extend through the electrosurgical pencil hand piece Housing, and into the interior of the Cabinet. Pressing the Buttons from the exterior of the Pencil allows current to flow through the conductors of the First Frame and the Second Frame to an active electrode placed at the end of the Pencil, which electrode carries current, as selected by the surgeon, to the patent.

The metal Frames of the present invention are preferably formed from two reels of conductive sheet metal. Each reel is comprised of a long flat ribbon of metal of indefinite length, generally rolled onto a spindle for ease of handling. The reels are long enough to allow many Frames to be cut, by stamping or punching, in a long row using either flat or rotary die. In the preferred cutting operation, the reels are oriented in relation to the cutting die so that the width of the reels is sufficient to accommodate the full length of the Frames, plus supporting material. The result of the cutting operation is two long reels of connected, cut First Frames and Second Frames, each such Frames formed in the configurations described below.

The metal sheet of the Frames is thick enough and conductive enough to carry current sufficient to cut, coagulate, ablate, excise, cauterize, or seal tissues by application of electric current to biological tissue through an active electrode. The Frames, once stamped, form unitary conducting strips, with holes and tabs formed to create operable portions, which provide an electrical connection between the contact leads from an electrosurgical generator to an active, cutting electrode. As this invention utilizes two kinds of Frames, one for the Top and one for the Bottom, two ribbons rolled on to two reels, with separate stamping die operations for each reel, produce two different reels of stamped metal parts.

Turning initially to the First Frames, the each First Frame in a first reel is stamped so as to create two Activation Straps from portions of the First Frame intended to be active components of the Switch circuitry. These Activation Straps are bent to serve as one side (the first side, within the Tops of each Switch) of the contacts within the Switch intended to make the electrical connection from the generator to the active electrode when the surgeon activates the Buttons of the Pencil. To accomplish the spring action, each Spring Contact is cut from the First Frame so as to leave a strip of metal which may act as a spring. These strips, which may have wide sections midway along their length as "landings" for contact with Buttons and for enhanced electrical contact, are then pressed into shape, with small bends at either end and toward the middle, thereby creating two Spring Contact strips having spring action within the First Frame.

The Activation Straps provide resistance to closing the circuit between the First Frame and the Second Frame. However, when pressure is applied to a Spring Contact during a surgical procedure, that Spring Contact may be compressed, or depressed, sufficiently to close the electrical connection between the First Frame and the Second Frame. Such closure allows current to flow from the generator leads, through one Frame, to the other Frame via the Spring Contact, and on to the active electrode. The Activation Straps may be formed of different materials and thickness to provide a variety of circuit closing resistances, thereby allowing the manufacturer, based on user preferences, to design in a variety of forces necessary to close the circuits between conducting strips. They may therefore be "tuned," as desirable, to provide different tactile forces by simple changes in the stamping die, and changing the "width" of the Activation Straps of the First Frame.

The First Frame is also stamped with tabs at each end. The tabs may be bent, pressed, or crimped into shapes which may coact with the active electrode at the "front" end of the First Frame and, in one embodiment of the present invention, with wire conductors which connect to the generator at the "back" end of the First Frame. More specifically, at the front end of the First Frame, the tab is generally crimped to form a tubular end, for receiving the active electrode, and within which the active electrode may be inserted to make electrical contact between the First Frame and the active electrode. At the back end of the First Frame, the tab is bent to create an insulation displacement connector, by which one wire lead from the electrosurgical. generator may be connected to the First Frame.

Turning next to the Second Frames, each Second Frame in a second reel is stamped so as to create two conducting strips from portions of the First Frame. These are also intended to be active components of the Switch circuitry. Small, substantially circular sections of these conducting strips are bent or pressed near their front ends into hemispherical or "dome" shaped elements ("Domes"), which are intended to serve as the second side of the contacts within the Switch intended to make the electrical connection from the generator to the active electrode when the surgeon activates the Bottons of the Pencil.

The two conducting strips of the Second Frame are also stamped with tabs at their back ends. As with the First Frame, the tabs at the back ends of the two conducting strips may be bent or pressed into shapes which may coact with the wire conductors which connect to the generator at the "back" end of the Second Frame. More specifically, the tabs at the back ends of the conducting strips of the Second Frame are bent to create (at least) two insulation displacement connectors, by which (at least) two wire leads from the electrosurgical generator may be connected to the Second Frame. In the normal mode, both the initial cutting of the First and Second Frames, and the bending and folding to create Activation Straps, bent tabs, Domes, and other features of the Frames, may be accomplished in a single or continuous stamping (for each reel of Frames).

When initially formed, the First Frames and the Second Frames of each reel of Frames remain physically connected to the reels, and so to each other. Eventually, the Frames of each reel will be separated from the reels, and some connecting portions of the reel will eventually be discarded. However, immediately after the reels are first stamped, narrow portions of the reel secure each Frame to adjoining Frames, generally though surrounding metal of the reel which will eventually be cut away. Each of these narrow portions of reels are narrow necks of metal connecting two larger metal areas, much as an isthmus of land connects to larger areas of land. In this application, these narrow necks of metal connecting two larger metal areas are termed "Isthmus." Until the Isthmus are cut, thereby releasing the Frames from the reels, the physical support provided by the Isthmus between the Frames and the remainder of the reels allow the First Frames of one reel and the Second Frames of the other reel to be handled as a unit.

Focusing on individual Frames, a Top (consisting of First Frame and surrounding plastic) may be formed by setting a First Frame into a mold, and then pouring plastic into the mold. In this process, a Frame is positioned in a mold, and suitable insulative material, generally plastic, is injected into the mold so as to embed, in a molded base, certain portions of the Frames. By "over molding" in this fashion, a First Frame may be partially enclosed within plastic which is designed to hold the First Frame, and also designed to join with complimentarily shaped plastic from a corresponding Bottom. A Bottom, in turn, is formed by over molding a Second Frame. In over molding the Top and the Bottom, the molds in each case are shaped so that Activation Straps, Domes, and much of the tabs which form insulation displacement connectors and the tubular section for holding an active electrode, remain uncovered by plastic. Each of these elements must be easily accessed to complete the electrical circuits of the Switch within the Cabinet. The molded plastic of the Tops and Bottoms insulates the Frames electrically, except where the Activation Straps, Domes, and tabs are open for contact.

Once the Frames have been over-molded, the Frames mainly reside inside the Tops and Bottoms (except for the active components which must be reached electrically), while the portions of reels to be discarded, including most of the Isthmus connecting the Frames, hang over, or outside the perimeter of, the molded plastic bases. The plastic of the Tops and Bottoms is also formed with channels along two of their exterior sides, which channels narrow the Cabinets at the points where the Frame Isthmus protrude. This narrowing allows insertion of a cutter or punch into the close fit between adjacent Tops and adjacent Bottoms, while cutting of the Isthmus from the assembled Cabinets during manufacture. The plastic of the Tops and Bottoms is also formed with pins and matching holes at appropriate points along their length, for holding the Tops and Bottoms tightly together once they are joined and pressed together. In the alternative, the plastic of the Tops or the Bottoms (or both) may be formed with "ribs" on their outer edges, which ribs may be inserted into matching channels on the other component of the Cabinet (Bottom or Top), to hold the Top and Bottom of a Cabinet together once they are pressed together. Whether the Top and Bottom of a Cabinet is held by "pin to hole" parts on each half, or by "rib to channel" parts, these methods achieve a "snap fit" when these components are pressed together, thereby keeping the two parts tightly joined. During assembly, the Tops are positioned by the pins and holes of the Top and Bottom, so that the Activation Straps of the First Frame are centered on the Domes of the Second Frame.

To create individual Cabinets from two reels of Cabinets (overmolded First and Second Frames), the Top and Bottom of one Cabinet along the reels may be separated from other Tops and Bottoms of other Cabinets. This may be accomplished by separating First Frames one from another on one reel, by cutting the Isthmus between them, and by separating Second Frames one from another on another reel, by cutting the Isthmus between them. First Frame Isthmus and Second Frame Isthmus may be cut together, in a single punch operation, and this is the preferred method. Separating Cabinets in this way allows the Cabinets to be removed from portions of the reel which will not be used (but may be recycled). Separating Cabinets in this way also allows the automated machinery to catch the Cabinets, and move them to the next stage in the automated assembly process.

Wire generator conductors, which will be used to connect the Switch to the generator, may be inserted between the insulation displacement connectors of the First Frame and the, insulation displacement connectors of the Second Frame, at the back end of the Cabinet. Joinder of the wire generator conductors to the Tops and Bottoms of the Cabinets generally takes place, in a process described more fully below, after the Frames are over-molded, and before the Tops and Bottoms are joined. The wire generator conductors are part of cable assemblies having multiple-prong plugs at one end of the assemblies, and conductor ends at the other end of the assemblies. These cable assemblies are attached to a first halves of the Switch Cabinets (generally the Tops), and the other halves of Switch Cabinets (generally the Bottoms) are pressed onto the first halves, in order to permanently join the cable assemblies to the Cabinets.

Taking now individual, separated, Cabinets, each of the generator conductors, which are often three in number (and are three in one preferred embodiment of this invention), are electrically connected to a connector plug that insert into a generator, to supply current to the Frames of the Switch. To make these connections, the generator conductors are cut to a fixed length in an automatic cutting machine. The generator conductors are then positioned in three "channels" in the Top, thereby making contact with the insulation displacement connectors of the First Frame, the channels acting as a guide to hold the generator conductors. This positioning of generator conductors holds the three generator conductors in very tight tolerance positions, necessary for accurately joining the Top and the Bottom of the Cabinet.

Once the Top and Bottom are joined, with First Frame and Second Frame residing within the closed Cabinet, the connecting wires, held in place by the insulation displacement connectors of the Frames, extend from the proximal end of the Switch, and the tubular end of the metal frame extends from the distal end of the Switch.

Once the wire conductors are in place, any one Cabinet is ready for (hand or automated) insertion into a Housing, as the next step in assembling a Pencil. The process of inserting a Cabinet into a Housing is made easy by forming the Housing and Cabinet in such a way as to allow insertion of the Cabinet into the end of the Housing, and require a tight mating of the Cabinet within the Housing. In particular, the Cabinet is formed from plastic, of any suitable composition, in a generally long, slender "box" having uniform dimensions side to side, and top to bottom, and without appreciable irregularities in its exterior. Such uniformity in the Cabinet dimensions and exterior are desirable in a Switch which is intended to be inserted into one end of a Pencil Housing, slid into proper operating position, and pressed or "snapped" into place within the Housing.

The Pencil exterior is best formed in two injection molded pieces: a Housing, with apertures at either end, and a closure means. ("Cap") for sealing one of the Housing end apertures. As noted above, one aperture, at the font of the Housing, is intended to receive the crimped tubular end of the Switch metal First Frame. The front aperture is therefore formed to snugly receive that tubular end. The "back" end aperture, toward the generator and away from the workpiece when in operation, is formed for engagement with the Cap closure means. The back end aperture may also be formed to allow access to the interior of the Housing by the generator conductors. These features at the back end of the Housing main body will be discussed more fully below, after first a discussion of the interior features of the Housing which allow automated assembly of Switch Cabinet and Housing.

The front end interior of the Housing is formed to securely engage the Switch Cabinet once it is inserted into the Housing. Accordingly, a portion of the housing is formed with an interior the same size as, or just larger than, the Cabinet. The goal here is to firmly hold the Cabinet within the Housing, without material clearance between Cabinet and Housing for vibration, or "play," between these components. In one embodiment, the Cabinet is formed with small protrusions which may bear against one or more of the sides, top, or bottom, and deformed as the Cabinet is pressed into position within the Housing. In the alternative, these protrusions may be formed on one or more interior surfaces of the Housing, and a standard Cabinet (i.e., without protrusions) used. The protrusions, whether formed on the Cabinet or on the interior of the Housing, provide a "compression fit" of the Switch within the Housing after the Cabinet is pressed into final position within the Housing during assembly.

The section of the Housing just back of the front end of the Housing is also formed with a "stop" or "seat," up against which the Cabinet is pressed during assembly, and against which the Cabinet may be seated, and thereafter reside, after the Cap is fitted over the back end aperture of the Housing to close the Housing around the Cabinet. The placement of the stop may vary, however the stop is generally formed to allow the Cabinet to slide forward in the Housing during assembly sufficiently far to allow the crimped tubular end of the Switch metal frame to extend to or from the front end aperture of the Housing. The Cabinet, within which the Switch resides, and the stop, are each formed to closely engage one another, and the Cabinet edges and stop corners may each be rounded by adding a radius, or increasing the existing radius, to reduce strain and insure proper seating of the Cabinet against the stop within the Housing.

Toward the back end aperture, away from and rear of the stop, the interior of the Housing may be differentially widened, to allow easy, fully automated, insertion of the Cabinet within the Housing during assembly. In the alternative, and for the same purpose, the interior of the Housing may be uniform in dimensions (height and width) generally, and significantly larger than the Cabinet, and small tracks or ramps formed within the interior of the Housing. Such small tracks or ramps may begin at the interior surface of the interior of the Housing at or near the back end aperture, and they may increase in height as they approach the stop. With either of these constructions, a Cabinet may be inserted into the back end aperture of a Housing, and slid up to and against the stop, as the interior of the Housing, or the tracks or ramps within the interior, close around the Cabinet snugly, to keep the Cabinet positioned within the Housing.

At the back end of the Housing, the back end aperture, though which the Cabinet is inserted during assembly, is formed to receive and hold a Cap. This may be accomplished in a variety of ways, however one construction which results in a clean exterior look for the closed Housing, is to undercut the exterior side of the Housing for a short distance around the back end aperture, so a Cap may be slid in place over the undercut area of the Housing. The thickness of the Cap and the depth of undercut of the Housing may be matched to produce a smooth seam between these components. The Cap may also be held in place over the aperture of the Housing in a variety of ways, however one construction which results in closure conducive to automated assembly is to form a circumferential groove, within the undercut area of the Housing, with which a matching circumferential bump or rib formed in the Cap near its opening may engage. Of course, the circumferential bump or rib may be formed within the undercut area of the Housing, with which a matching circumferential groove formed in the Cap may engage, with the same "locking" effect between the Cap and the Housing, as the opening of the Cap engages with the aperture of the Housing.

A similar locking effect may be achieved by forming one or more, non-circumferential, matching dimples and bumps in these same areas of the Cap and the Housing (dimples on the exterior of the undercut Housing and matching bumps on the interior of the Cap, or bumps on the exterior of the undercut Housing and matching dimples on the interior of the Cap). The undercut area of the Housing and the matching surface of the interior of the Cap may also be beveled, to allow easy centering of the Cap over the aperture of the Housing, and tight fit of the Cap over the aperture when the Cap is pressed in place, and the bumps and grooves (or dimples) "snap" together as they engage.

Some portion of the Housing may be formed with a Housing slit, into which the generator conductors may be placed as the Cabinet is inserted into the Housing, and the Cap placed over the back end aperture to complete assembly of the of the Housing and Cap. The slit, if present, is formed near the back end aperture, and generally within the undercut area of the Housing, and on the bottom side of the Housing, so the generator conductors are seen less and felt less by a user. The slit, if present, runs generally from the aperture edge to the toward the front aperture. The slit, if present, is also wide enough to allow access for the generator conductors without undue pressure, but narrow enough at its end to hold the conductors without undue play. The slit, if present, may be tapered, to allow easy, fully automated centering and placement of the generator conductors into the slit when the Cabinet, to which the conductors are attached, is placed into the back end aperture, and slid forward toward the Cabinet stop within the Housing.

The Cabinet is also provided with activation openings centered over each Spring Contact, and exposing a portion of each Spring Contact at the bottom of its well, such exposure being substantially over the center of each Spring Contact. Via these Cover openings, one may, using an appropriately shaped component, such as an elongate stem extending from one of the activation Buttons on the exterior of the Pencil, apply pressure to the Activation Straps (generally one at a time). Such pressure causes the Activation Straps to depress until they close the contact between the First Frame and the Second Frame. This closure completes the electrical circuit selected by the surgeon when she presses one (generally) of the Buttons, thereby causing the Button stem to extend into and through the activation opening for that Button, and against the top of the Spring Contact appropriate for closure of the desired circuit. At the same time, the depressed Spring Contact, or the component used to apply pressure to the Spring Contact, or both of these elements, may produce an audible "click" when depressed which, when added to the break in mechanical resistance of the Spring Contact as it pops into "closed" position, reinforces the feedback given the surgeon about the (electrically active or passive) status of the Pencil.

The entire exterior surface of the Housing may be formed to be smooth, or with ridges or other features, to provide a desirable tactile feel for the user. The overall dimensions of the Housing may be varied, within the constraints imposed by the exterior dimensions of the Cabinet, to provide a variety of "grips," "hefts," "weights," "looks," or "feels." The Housing is also formed with openings, generally two in number, over which buttons having stems may be positioned, again using automated machinery, and into which the stems may be inserted. These openings are positioned over corresponding openings within the Cabinet once the Cabinet is finally positioned within the Housing, and pressed into place. Accordingly, the stems of the buttons, when the buttons are properly positioned and pressed into place, will extend to a position directly over or touching the Activation Straps within the Cabinet (which then make and break contact for the Switch).

The Cap of the present invention, by which the Housing is closed, is also formed for automated assembly. More specifically, the Cap, which may be injection molded plastic, is formed so that it may be held by automated machinery, and yet, in the best embodiment, is formed with a smooth exterior, having ridges, and a variety of "grips," "hefts," "weights," "looks," or "feels," which may match the exterior of the Housing. As noted above, the Cap may also be held in place over the aperture of the Housing by a circumferential bump formed in the Cap (with matching circumferential groove within the undercut area of the Housing), or by a circumferential groove in the Cap (with matching circumferential bump or rib within the undercut area of the Housing), by which the Cap and the Housing may engage, to achieve a locking effect between the Cap and the Housing. Once the Cap and Housing are locked to one another in this way, at least one face at the opening of the Cap is generally tightly seated against a corresponding face formed at or near the back end aperture of the Housing, thereby smoothly (and tightly) closing the Cap to the Housing.

Some portion of the Cap may be formed with a Cap slit, which matches positionally, and coacts with, the Housing slit. The slit, if present, is formed near the open end of the Cap, and on the bottom side of the Housing, so the generator conductors are seen less and felt less by a user. The slit, if present, is also wide enough to allow access for the generator conductors without undue pressure, but narrow enough at its end to hold the conductors without undue play. The slit, if present, may be tapered, to allow easy, fully automated centering and placement of the generator conductors into the slit when the Cap is positioned over the back end aperture of the Housing, and slid forward on to the undercut area of the Housing (and "snapped" into place as the closure means engage).

The generator conductors may also pass through a hole formed in the Cap, preferably at approximately its center so the conductors travel axially within the Cap, as an alternative to forming matching slits in the Housing and Cap for entry of the conductors into the Housing from the generator. Since the Cap will be formed separately from the conductors, the conductors must be passed through such a hold in the Cap before either the contact ends are secured to one end of the conductors, or before the other ends of the conductors are secured to the Switch within the Cabinet. The primary benefit to be derived from a centered conductor opening is a sleeker design, however some manufacturing efficiency may be lost with this design.

Once the Cabinet is pressed into its final position within the Housing, an active electrode may be inserted into the crimped tubular end of the Switch First Frame, which extends from the "front" of the Cabinet. The tubular end of the Switch is formed to fit snugly through an aperture at the corresponding "front" end of the Housing. The crimped tubular end of the Switch metal frame may extend from the front of the Housing once it is finally positioned within the Housing, or it may reside entirely within the front end of the Housing, and the active electrode cutting blade inserted into the aperture, and the crimped tubular end of the Switch metal frame within the aperture. The active electrode, or cutting blade, may be finally positioned during manufacture of the Pencil, or thereafter, by a user wishing to change active electrode blades. However, in any case the crimped tubular end of the Switch metal frame extends from the Cabinet of the Switch toward the workpiece when the Switch is in final position within the Housing. The crimped tubular end of the Switch metal frame is also formed to fit snugly within the aperture, to reduce transmission of moisture to the interior of the Pencil when in use, and yet it is formed to slide easily into position within the aperture, so the crimped tubular end of the Switch is not bent during assembly of the Pencil.

In larger-scale manufacture, the forming and assembly of the components of Switches are multiplied, so that many Frames, Tops, and Bottoms may be formed in an assembly line of indeterminate length and speed. Essentially, a first reel of First Frames of indeterminate length are "loaded" into the front end of an automated assembly line of first molds that "over-mold" the line of First Frames of the first reel, thereby producing a line of finished Tops. A second reel of Second Frames of indeterminate length are loaded into the front end of an automated assembly line of second molds that over-mold the line of Second Frames of the second reel, thereby producing a line of finished Bottoms. The first and second molds may have any number of cavities for insertion of the Frames before molding, limited only by tool and machine size.

In this larger-scale manufacture, wire conductors from cable sub-assemblies are inserted between the insulation displacement connectors of the First Frames and the insulation displacement connectors of the Second. Frames at the appropriate point on the assembly line, after the First Frames and the Second Frames have been over-molded by the line of first molds and second molds, and before the Tops and Bottoms are joined. Cable assemblies, with plugs, then travel along with the completed Cabinets. However, in larger-scale manufacture, the separation of First Frames and separation of Second Frames by cutting the metal between them may be delayed, so that the Tops (First Frames and over-molded plastic) may continue to be handled as a unit on the assembly line, and the Bottoms (Second Frames and over-molded plastic) may continue to be handled as a unit on the assembly line. The delay in separation of Frames allows the joinder of the cable sub-assemblies to the Cabinets of the Switches "on line," so that the cable connectors are put in place between Tops and Bottoms on the assembly line, and the Tops and Bottoms are joined, before the Cabinets are separated. Immediately after separation of Cabinets, the automated insertion of the Cabinets into the Housings speeds the assembly process.

In separate, often parallel, assembly lines, a series of connected Pencil Housings are formed to fit snugly over the Cabinets once they are separated one from another, and a series of connected end closure Caps are formed to fit snugly over the rear aperture and lock in place. Once the Cabinets are inserted into the Housings on the assembly line, the already formed Caps may be automatically fitted to the rear apertures of the Housings and pressed into place. The connected Housings may be separated from each other, and connected Caps separated from each other, at any point in this process of assembly, however the later adjacent Housings and Caps are separated, the more automated a process may become generally. The Buttons may then be automatically pressed into their openings in the Housings, an active electrode fitted into the front aperture of the Housings, and the finished Pencils may be tested and packaged, all in line, in a fully automated process.

The full benefits of assembling electrosurgical pencil switches in this fashion may be gained by automating the entire assembly process, and extending the process to assemble many Switches simultaneously. The apparatus of the Switch is, in fact, designed to lend itself to just such multiple Switch assembling. To accomplish this, fully automated machinery may be employed to form and handle arrays of components, and position and secure the components of the arrays to each other, through every step of the process of Switch and Pencil assembly. In such larger-scale manufacture, as noted above, an array of identical multiple Frames may be formed from a larger reel of sheet metal, in a multiple-frame configuration, in which all Frames, with all electrical conductors, are and remain part of the same metal sheet (until they are later cut as described herein). In this configuration, Frames are physically and electrically connected to adjacent Frames, in arrays of Frames. The arrays of Frames may then be positioned, as arrays, into molds designed to form arrays of molded Tops and Bottoms. Suitable insulative material may be poured into the array molds so as to embed, within the arrays of Tops and Bottoms, almost all non-moving portions of the Frames. In this position, the Frames reside largely within the insulative material in both Tops and Bottoms, while the portions of the Frames to be discarded reside outside the insulative material of the Tops and Bottoms.

Continuing with larger-scale manufacture. An array of Tops, formed in an array mold as described above, may then be placed over and array of Bottoms, similarly formed. To compete assembly of the array of Cabinets, an array of connecting wires, which may be previously cut to a fixed length in an automatic cutting machine, may then be grouped for each Cabinet within the Cabinet, and positioned to be accepted by the array of Tops and Bottoms, and the array of grouped wires pressed into the channels of the Tops or Bottoms, and the arrays Tops and Bottoms closed to form an array of Cabinets. By such assembly, all connecting wires of each Switch within the array of Cabinets, through its corresponding insulation displacement connectors, is electrically connected to its own connecting wires, and each connecting wire is held against separation from its corresponding insulation displacement connector. However, a portion of the Frames, the exterior most portions of the Frames outside the insulative material of the Tops and Bottoms, extends between adjacent closed Cabinets.

Continuing with larger-scale manufacture, an array of cutters or punches formed to extend into channels on the sides of the Tops and Bottoms, or merely close along the sides of the Cabinets once the Tops are joined to the Bottoms, may be deployed on an array of Cabinets, to cut the materials between Cabinets throughout an array of Cabinets, or along the joined line of Cabinets if Frames have been formed on reels. Simultaneous cutting of such material, or "rolling" (continuous) cutting of such material if the Frames have been formed on reels, allows the Cabinets within an array to be separated from one another in a single (or continuous) cutting operation.

In a second embodiment of the present invention, the main components of the Switch of the present invention may be formed to produce a lower cost version of the Switch and Cabinet of the present invention, along with corresponding exterior Pencil hand piece Housing members, and high quality electrical generator conductors. Such Housing members and conductors are formed to be easily and securely attached and separated from the hand piece of the Pencil, largely by modification of joinder of the Cap to the Housing.

In this second embodiment, the Switch is still comprised in part of a First Frame, molded integrally within top plastic to form the Switch Top, and a Second Frame, molded integrally within bottom plastic to form the Switch Bottom. The Switch, once assembled, are still inserted into an insulated surgical pencil Housing. However, the wire generator conductors, by which the generator is electrically connected to the Frames, terminate within a Cap formed to be reusable, and the Cap, generator conductors, and plug of the plug assembly, which now form a single "Cap and Cable Assembly," are each reused. This new arrangement for a surgical pencil requires somewhat minor modification in the Frames (and therefore the plastic which, together with the Frames, forms the Tops and the Bottoms of the Cabinet), and larger modifications of the Housing and Cap. In addition, the closure of the Housing with the Cap may be made in such a way is to indicate the joinder of the Cap to the Housing is complete, and secure. This second embodiment will be explained by reference to the components of the first embodiment, and how those components must be varied to accomplish the intended goals for the second embodiment.

Beginning with the Frames of the second embodiment of the Switch, both the First Frame and the Second Frame may be shorted in length over the length of the First and Second Frames of the first embodiment, by reducing the length of the tabs at the rear (proximal) end of the Frames. Since insulation displacement connectors are not necessary in this second version of the invention, the bending of tabs at the rear of the Frames, and so the additional length for those tabs, is also not necessary. In addition, a shorter Cabinet Switch overall allows more of the Cap, formed as set forth in detail below, to be inserted within the Housing, thereby providing a more solid joinder between Housing and Cap. The metal Frames are again preferably formed from two reels of conductive sheet metal, each reel is comprised of a long flat ribbon of metal, generally rolled onto a spindle for ease of handling.

The result of stamping the First and Second Frames of this second embodiment of the present invention is again two long reels of connected, stamped Frames, each adjacent Frame configured as in the first embodiment except for the arrangement of the tabs at the rear of the Frames. As to the tabs specifically, they are bent during stamping so as to create a lending for electrical contact. This landing will bend when the Housing (with its internal Switch after assembly) and the Cap are joined and twisted, in a process more fully explained below.

In this second embodiment, the Frames are again over-molded, so that the Frames mainly reside inside the Tops and Bottoms (except for the active components which must be reached electrically), while the portions of reels to be discarded, including most of the Isthmus connecting the Frames, hang over, or outside the perimeter of, the molded bases. The plastic of the Tops and Bottoms is also formed with channels along two of their exterior sides, which channels narrow the Cabinets at the points where the Frame Isthmus protrude, to allow each separation of Cabinets. Again, the plastic of the Tops and Bottoms is formed with pins and matching holes at appropriate points along their length, for holding the Tops and Bottoms tightly together once they are joined and pressed together and, during assembly, the Tops are positioned over the Bottoms by the pins and holes of the Tops and Bottoms, so that the Spring Contacts of the First Frames are centered on the Domes of the Second Frames. The Tops and Bottoms of Cabinets may again be separated from other Tops and Bottoms by cutting the Frame Isthmus.

However, in this second embodiment, wire generator conductors are not then inserted between Tops and Bottoms before their joinder, and separation into individual Cabinets. Rather, these conductors are incorporated into the Housing closure Cap, in the fashion described below. The wire generator conductors then become part of a cable assembly with a multiple prong plug at one end, and the Cap (with enclosed conductors) at the other end. This "Cap and Cable Assembly" is then provided to the end user, generally as part of a package of one Cap and Cable Assembly and many Housings containing Switches.

In this second embodiment of the invention, each Cabinet, once closed, and with bendable and resilient tabs extending from the rear thereof, is inserted into a Housing, using the features of the front end of the Housing set forth for the first embodiment, and again pressed or "snapped" into place within the Housing. These front end Housing features include the tracks upon which the Switch Cabinet may slide within the Housing, the ramps for positioning the Cabinet on the protrusions, and the stop against which the Cabinet bears once the Switch is pressed into place within the Housing. It should be noted, however, that the tracks and ramps for positioning the Cabinet within the Housing may also be shortened, to substantially match the overall length of the Cabinet. This shortening allows the interior of the Housing of this second embodiment to be smooth and substantially circular in cross section at its rear end, so that the substantially circular in cross section Cap of the Cap and Cable Assembly can be twisted within the Housing once the Cap is inserted into the Housing. Since the Cap must snugly engage the interior of the Housing in this embodiment, the interior of the Housing toward the back end aperture may not be differentially widened to allow easy insertion of the Cabinet. Again, a front aperture, at the font of the Housing, is formed to snugly receive the crimped tubular end of the Switch metal Frame.

The rear end of the Housing, in the other hand, must be modified in ways to accommodate the Cap and Cable Assembly. Firstly, the Housing may be shorted somewhat because the Switch Cabinet is shorter, so long as the Housing remains sufficiently long to accommodate the length of that portion of the Cap intended to be inserted into the Housing. Secondly, the back end aperture is formed with a slot, in the form of a "j," which allows a pin or tab on the Cap to travel within the slot, and be moved into a locking position with a twist of the Cap within the Housing. Other means for locking the Cap within the Housing may be utilized, however this particular use of a "j" slot allows one who is inserting the Cap within the Housing to easily confirm the Cap is in the correctly locked position within the Housing as explained below.

The Cap in the second embodiment of this invention is securely affixed around at least three pins which may engage the leads or tabs at the rear of the Frames extending from the Cabinets once they are positioned within the Housings. The at least three pins in turn are securely connected electrically to the wire generator conductors, which then extend from the main body of the Cap, and on to the Plug of the Cap and Cable Assembly. The joinder between the body of the Cap and the generator conductors is water-tight and secure, and the length between the end of the Cap and the Plug is typically about three meters, however it may be of any length. Each of the components of the Cap and Cable Assembly are of high grade materials, so that they may be sterilized in an autoclave and reused.

The Cap main body may be formed from a "first shot" of suitable plastic in one color, which is then over-molded with a "second shot" of suitable plastic, often of a different color. In one preferred embodiment the "first shot" is molded in green plastic, while the second shot is molded in blue plastic. The function of the green plastic in the first shot is to provide an indicator to a user that the Cap is correctly positioned on the Housing of the Pencil once the Housing and Cap are joined. One function of the blue plastic of the second shot of the over-mold is cosmetic. However, the over-mold, regardless of its color, bonds the main body of the Cap to the cable, and also provides a moisture barrier against the entry of fluids into the Cap. Since one end of the Cap must fit within the end of a Housing with circular cross section, the end of the Cap so fitting must also be substantially circular in cross section. With both pieces so formed, the Cap may rotate smoothly within the end of the Housing.

As with the first embodiment, once the Cabinet is pressed into its final position within the Housing, an active electrode may be inserted into the crimped tubular end of the Switch First Frame, which extends from the "front" of the Cabinet. The tubular end of the Switch is formed to fit snugly through an aperture at the corresponding "front" end of the Housing. The crimped tubular end of the Switch metal frame may extend from the front of the Housing once it is finally positioned within the Housing, or it may reside entirely within the front end of the Housing, and the active electrode cutting blade inserted into the aperture, and the crimped tubular end of the Switch metal frame within the aperture. The active electrode, or cutting blade, may be finally positioned during manufacture of the Pencil, or thereafter, by a user wishing to change active electrode blades. However, in any case, the crimped tubular end of the Switch metal frame extends from the Cabinet of the Switch toward the workpiece when the Switch is in final position within the Housing. The crimped tubular end of the Switch metal frame is also formed to fit snugly within the aperture, to reduce transmission of moisture to the interior of the Pencil when in use, and yet it is formed to slide easily into position within the aperture, so the crimped tubular end of the Switch is not bent during assembly of the Pencil.

The substantial benefits of the second embodiment of the present invention may be seen when numerous Pencil Housings, each with its own Cabinet and enclosed Switch is paired with a single Cap and Cable Assembly. When in use, a user may join a first inexpensive Housing with a first Cap by inserting the end of the Cap with circular cross section into the rear end of the Housing (which has been formed to accommodate the end of the Cap of the Cap and Cable Assembly). Once fully inserted into the Housing, the Cap end may be rotated or twisted within the Housing to bring the three pins of the Cap to engage, and bear up against, the leads or tabs at the rear of the Frames. This contact completes the connection between the Cap and Cable Assembly and the Frames within the Switch.

Rotating the end of the Plug within the Housing also allows an extension from the Cap, generally in the form of a pin or tab of plastic, to first slide down the length of the "j" slot at the back end aperture of the Housing, as the end of the Cap is inserted within the back end aperture, and then rotated within the bottom of the "j" slot, as the end of the Cap is rotated within the Housing, so that the pin or tab of the Cap is moved into a locking position within the Housing "j" slot. Once the Cap is correctly inserted within the Housing and locked into position, a user may then visually inspect the area near the joinder of the Cap and Housing, and see there, in the area of the top of the "j" slot, the green color of the plastic of the Cap main body "first shot." The user may then be assured that the Pencil so assembled is correctly and securely assembled, active, and ready for use.

However, as noted above, the benefits of the second embodiment of the present invention are gained when numerous Pencil Housings, each with its own Cabinet and enclosed Switch is paired with a single Cap and Cable Assembly. Accordingly, when a surgery is complete, or when the user so desires, the user may disengage the Housing of the Pencil from the Cap of the Cap and Cable Assembly, discard the used Housing, with interior Switch (and, likely, the active electrode still attached), and then re-engage the Cap of the Cap and Cable Assembly with a second Pencil Housing in the way described above. In this way, the user discards the first inexpensive Pencil hand piece, and retains and reuses the (relatively) expensive Cap and Cable Assembly for use with other inexpensive Pencil hand pieces.

The more important features of the invention have thus been outlined, rather broadly, so that the detailed description thereof that follows may be better understood, and in order that the present contribution to the art may be better appreciated. Additional features of specific embodiments of the invention will be described below. However, before explaining preferred embodiments of the invention in detail, it may be noted briefly that the present invention substantially departs from pre-existing apparatus and methods of the prior art, and in so doing provides the user with the highly desirable ability to multiply assemble electrosurgical pencil switches using the metal conductive components of the Switches to hold components, while other components are formed, positioned, and fastened in place. Such mass handling allows the assembly of such multiple switches, and even entire pencils, using automated machinery, without requiring human attention, except to maintain the automated machinery, and "feed" it with fresh components in bulk.

Objects of the Invention

One object and advantage of this invention is production of switches for electrosurgical pencils in a highly efficient, very cost effective, fully automated process, with entirely automatic equipment.

Another object and advantage of this invention is production of switches and electrosurgical pencils having improved safety and reliability.

Another object and advantage of this invention is production of switches and electrosurgical pencils having flexibility and choice activation force, or spring "action," electrical resistance, and audible circuit closure feedback.

Another object and advantage of this invention is production of switches and electrosurgical pencils having a limited number of parts, which are easily assembled.

Another object and advantage of this invention is production of switches and electrosurgical pencils having high quality electrical conductors, which may be reused many times with low cost replacement Pencils, at significant cost savings and reduced medical waste.

Another object and advantage of this invention is production of inexpensive switches and electrosurgical pencils which may be discarded as surgical waste after only a single use, thereby eliminating the cost of further handling, such as sterilization, and reducing biological hazard.

Another object and advantage of this invention is production of switches and electrosurgical pencils in which high quality, reusable, electrical conductors, may be positively joined to low cost replacement Pencils, to create a stable Pencil configuration when in use.

Another object and advantage of this invention is production of an electrosurgical pencils which unambiguously indicates to a user when the inexpensive disposable pencil and switch is properly connected to the more expensive, reusable, high quality electrical conductors.

Another object and advantage of this invention is production of multiple electrosurgical pencils in a continuous process, beginning with reels of sheet metal for the electrical components, through the automated over molding of non-conductive holding and insulating components, and automated assembly of such pencils to their final usable form.

Other features and advantages of the present invention are stated in or apparent from a detailed description of presently preferred embodiments of the invention set forth below.

BRIEF DESCRIPTION OF DRAWINGS

The accompanying drawings, which are incorporated in and constitute a part of this specification, illustrate preferred embodiments of the present invention, and such drawings, together with the description set forth herein, serve to explain the principles of the invention.

FIG. 11 is a perspective view of the Housing of the Pencil shown in FIG. 8, viewed from a rear quarter of the Housing, in which a portion of the interior of the Housing, and some details of the Housing-to-Cap closure may be seen.

FIG. 12 is a foreshortened perspective view of a portion of the interior of the Housing of the Pencil shown in FIG. 8, viewed from a rear quarter of the Pencil, in which a view of the details at the front end interior of the Housing may be seen.

FIG. 13 is a rear quarter perspective cut away view drawing of the Pencil shown in FIG. 8, in which the first preferred embodiment of the Switch of the present invention may be seen fully inserted into the Housing, and pushed up against the stop within the Housing.

FIG. 14 is a cross section view drawing of the Pencil shown in FIG. 8, in which the Switch of the present invention may be seen fully inserted into the Housing, and seated against the stop within the Housing, with the opening of the Cap fully engaged over the back aperture of the Housing, and the Cap Extension holding the Switch against the Housing stop.

FIG. 15 is a cut away view of a portion of the Cap and back end aperture of the Housing, showing the interior of the back portion of the Pencil shown in FIG. 8, in which the details of the circumferential groove in the Cap and matching circumferential bump or rib within the undercut area of the Housing may be seen locked into position after assembly.

FIG. 20 is a perspective view drawing of the Housing shown in FIG. 19, in which the second embodiment of the Switch is being inserted into the back end aperture of the Housing.

DETAILED DESCRIPTION OF A FIRST PREFERRED EMBODIMENT

First Preferred Embodiment

Figure 1:
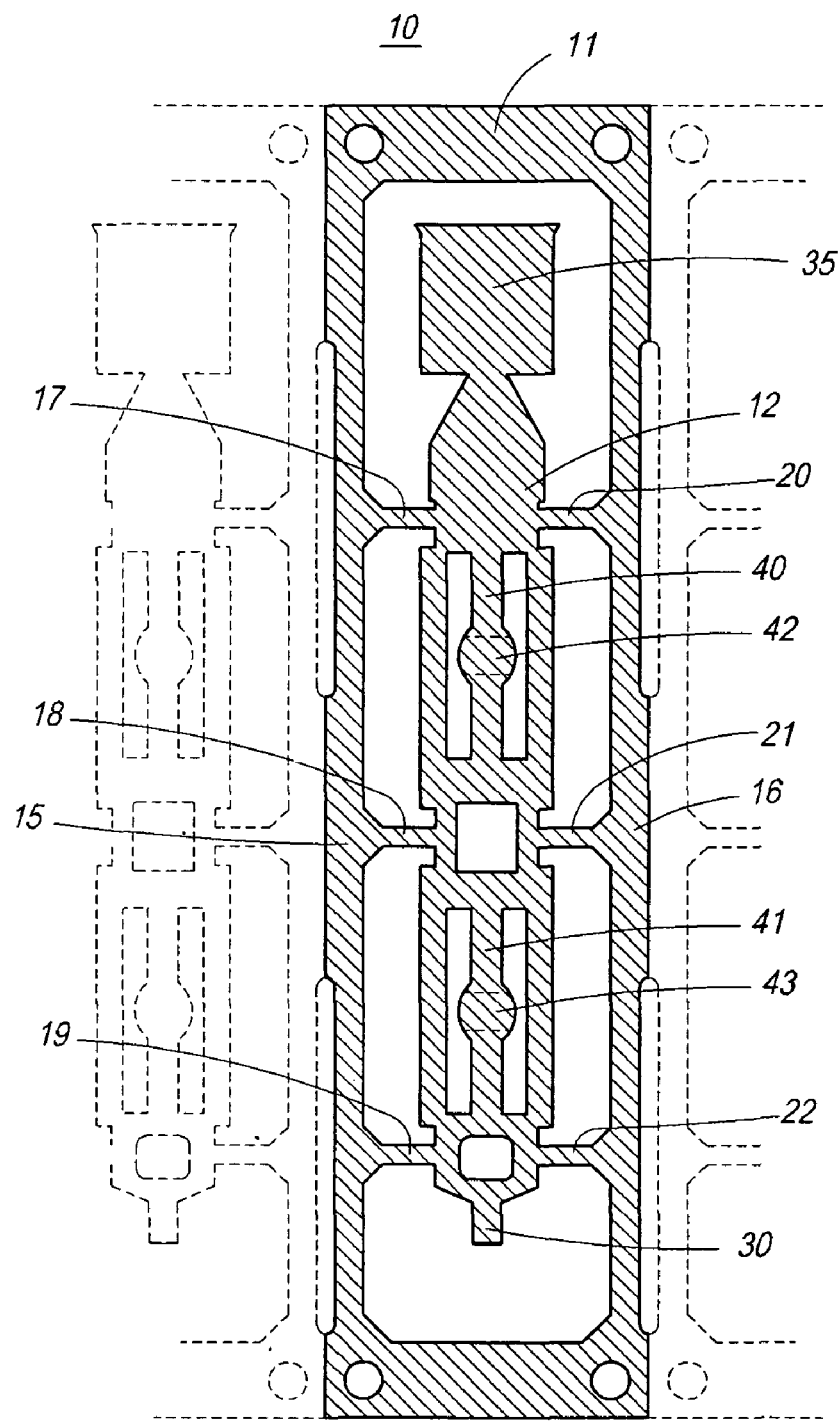
FIG. 1 is a plan view drawing of a first electrical circuit frame, seen connected to similar frames in a reel of such first frames, for a first preferred embodiment of the Switch of the present invention, viewed from the top of the frame.

Referring initially to FIG. 1, a first embodiment of an electrical circuit First Frame of the Switch of the present invention is shown in top down, plan view. In FIG. 1, First Frame 10 of the present invention is comprised of a unitary piece, formed from a blank sheet of conductive metal by stamping. The single sheet may be in the form of a reel of electrically conductive material. Portion 11 of frame 10, presented in cross-hatched rendering, is intended to be encased in an insulated Cabinet body (not shown). The metal sheet from which frame 10 is stamped is thick enough and conductive enough to carry current sufficient to cut, coagulate, ablate, excise, cauterize, or seal tissues by application of electric current to biological tissue through an active electrode (not shown). Frame 10, once stamped, forms a first conducting strip 12, which provides an electrical connection between two or more additional conducting strips stamped from a Second Frame (shown in FIG. 2), to thereby direct electrical current from an electrosurgical generator (not shown) to the active electrode.

As shown in FIG. 1, first conducting strip 12 is initially physically and electrically connected to First Frame 10 exterior portions 15 and 16 by narrow First Frame Isthmus 17, 18, 19, 20, 21, and 22. All Frame Isthmus will eventually be cut through, during assembly of the Switch, and exterior portions 15 and 16 of First Frame 10 discarded. In FIG. 1, the physical support provided by the Frame Isthmus 17, 18, 19, 20, 21, and 22 of between first conducting strip 12 and exterior portions 15 and 16 early in the Switch assembly process allows these components to be handled as a unit, until such time as these components are secured in the insulative molded Cabinet Top (not shown). Maintaining a physical unity of first conducting strip 12 and exterior portions 15 and 16 in this way allows production of the Switch in a fully automated process, by applying machinery to join First Frame 10 with corresponding molded plastic components (shown in later Figs.), and then separating first conducting strip 12 of metal frame 10 by cutting or punching Frame Isthmus 17, 18, 19, 20, 21, and 22 of First Frame 10.

FIG. 1 also shows first insulation displacement connector 30, which is intended to be an active component of the Switch circuitry once it is bent to serve as a contact for connecting to one of the leads from the electrosurgical generator (not shown). FIG. 1 also shows active electrode end tab 35, which is intended to hold the active electrode (not shown), and be an active component of the Switch circuitry once tab 35 is bent or crimped, as part of the stamping process, to form a tubular end for receiving the active electrode. FIG. 1. also shows two activation straps 40 and 41, which are cut into first conducting strip 12 during the initial stamping. The center landings 42 and 43 of activation straps 40 and 41 form substantially horizontal metal portions, against which a pressure may be exerted, to bend the activation straps 40 and 41 into electrical contact with underlying "dome contacts" (shown in FIG. 2). In this preferred embodiment, activation straps 40 and 41 are also crimped along their length so as to allow them to bend to make that electrical contact. The width of the activation straps 40 and 41, and the degree and method of their crimping, may be used to vary the amount of force necessary to deflect center landings 42 and 43 into contact with underlying dome contacts. These factors may also be varied to set the distance over which such force must be applied, and other factors which create a tactile feel for the user once the Switch has been fully assembled.

FIG. 1 also shows, in broken lines on either side of frame 10, where additional frames might be positioned in an array of identical multiple frames when such multiple metal frames are formed from a larger single metal reel. After an array of frames are stamped from such larger metal reel, all metal frames are part of the same metal sheet until they are separated one from the other by cutting or punching Frame Isthmus 17, 18, 19, 20, 21, and 22. In one preferred embodiment of the method of the present invention, such cutting and separation into individual metal frames may be delayed until all frames within an array of frames are fitted into a corresponding array of molded plastic components of the Switch, and assembly of the Switch is largely complete. After such fitting, then each frame 10 may be separated from each other metal frame by cutting them apart at Frame Isthmus 17, 18, 19, 20, 21, and 22, and all exterior portions 15 and 16 discarded.

Figure 2:
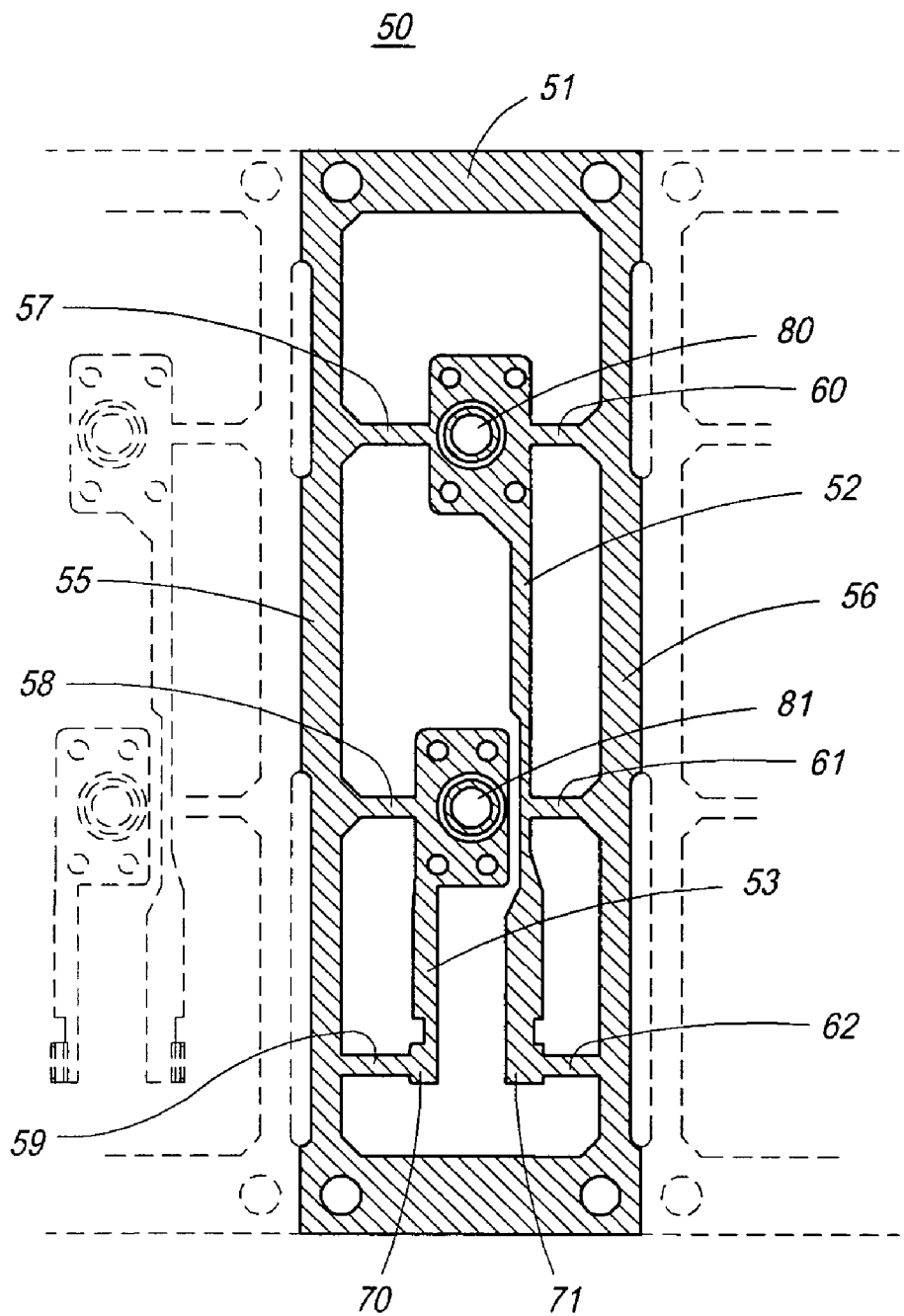
FIG. 2 is a plan view drawing of a second electrical circuit frame, seen connected to similar frames in a reel of such second frames, for the first preferred embodiment of the Switch of the present invention, again viewed from the top of the frame.

Turning now to FIG. 2, a first embodiment of an electrical circuit Second Frame of the Switch of the present invention is shown in top down, plan view. In FIG. 2, the Second Frame of the present invention 50 is comprised of a unitary piece, formed from a blank sheet of conductive metal by stamping. The single sheet may be in the form of a reel of electrically conductive material. Portion 51 of frame 50, presented in cross-hatched rendering, is intended to be encased in an insulated Cabinet body (not shown). The metal sheet from which frame 50 is stamped is thick enough and conductive enough to carry current sufficient to cut, coagulate, ablate, excise, cauterize, or seal tissues by application of electric current to biological tissue through an active electrode (not shown). Frame 50, once stamped, forms a second conducting strip 52 and a third conducting strip 53, each of which may provide an electrical connection between contact lead stamped from First Frame 10, to thereby direct electrical current from an electrosurgical generator (not shown) to the active electrode.

As shown in FIG. 2, second and third conducting strips 52 and 53 are initially physically and electrically connected to Second Frame 50 exterior portions 55 and 56 by narrow Second Frame Isthmus 57, 58, 59, 60, 61, and 62. All Frame Isthmus will eventually be cut through, during assembly of the Switch, and exterior portions 55 and 56 of Second Frame 50 discarded. In FIG. 2, the physical support provided by the Frame Isthmus 57, 58, 59, 60, 61, and 62 between second and third conducting strips 52 and 53 and exterior portions 55 and 56 early in the Switch assembly process allows these components to be handled as a unit, until such time as these components are secured in the insulative molded Cabinet Bottom (not shown). Maintaining a physical unity of second and third conducting strips 52 and 53 and exterior portions 55 and 56 in this way allows production of the Switch in a fully automated process, by applying machinery to join Second Frame 50 with corresponding molded plastic components (shown in later Figs.), and then separating second and third conducting strips 52 and 53 of metal frame 50 by cutting or punching Frame Isthmus 57, 58, 59, 60, 61, and 62 of Second Frame 50.

FIG. 2 also shows second and third insulation displacement connectors 70 and 71, which are intended to be an active component of the Switch circuitry once they are bent to serve as contacts for connecting to leads from the electrosurgical generator (not shown). FIG. 2 also shows two dome contacts 80 and 81, which are pressed into second and third conducting strips 52 and 53 during the initial stamping.

In operation, activation straps 40 and 41 may make, and may maintain, electrical contact with Second Conducting Strip 52 or Third Conducting Strip 53, at the surgeon's election. When a surgeon presses a button (shown in later figures) corresponding with the current and voltage desired for the task at hand, activation straps 40 and 41 may be bent or depressed so that center landings 42 and 43 may make electrical contact with either dome contact 80 or dome contact 81. By this action, the surgeon may choose to electrically activate Second Conducting Strip 52 or Third Conducting Strip 53, depending on whether cutting or coagulating is desired. By such activation, the circuit of choice, carrying the voltage desired by the surgeon is completed through the active electrode, and the patient, and back to the electrosurgical generator.

FIG. 2 also shows, in broken lines on either side of frame 50, where additional frames might be positioned in an array of identical multiple frames when such multiple metal frames are formed from a larger single metal reel. After an array of frames are stamped from such larger metal reel, all metal frames are part of the same metal sheet until they are separated one from the other by cutting or punching Frame Isthmus 57, 58, 59, 60, 61, and 62. In one preferred embodiment of the method of the present invention, such cutting and separation into individual metal frames may be delayed until all frames within an array of frames are fitted into a corresponding array of molded plastic components of the Switch, and assembly of the Switch is largely complete. After such fitting, then each frame 50 may be separated from each other metal frame by cutting them apart at Frame Isthmus 57, 58, 59, 60, 61, and 62, and all exterior portions 65 and 66 discarded.

Figure 3:
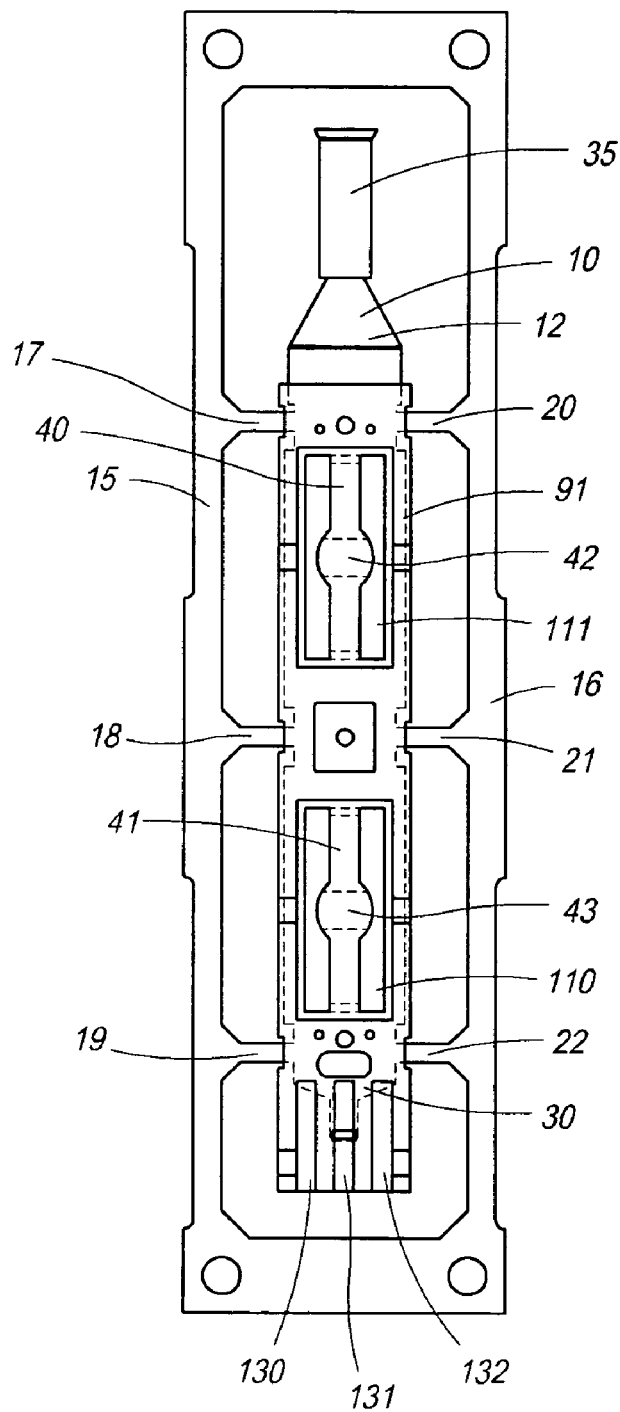
FIG. 3 is a plan view drawing of the first electrical circuit frame of FIG. 1, in which a Cabinet Top has been formed over the first frame by pouring of plastic into a first mold.

Turning now to FIG. 3, molded Cabinet Top 90 of the Switch of the present invention is shown in bottom up, plan view, prior to cutting through Frame Isthmus 17, 18, 19, 20, 21, and 22 to separate (and discard) exterior portions 15 and 16 from First frame 10. The Cabinet top molded base 91 (non-conductive exterior) is formed as a single piece, with conductive elements (the metal frame 10 of FIG. 1) embedded within. Molded base 91 may be viewed as one half of the full Switch Cabinet, with features of First Frame 10 within molded base 91 presented in dotted lines. To form Cabinet top, First Frame 10 is positioned in a mold (not shown) intended to shape base 91 by molding plastic, non-conductive compound around First Frame 10. Once in such position within such mold, suitable insulative material, generally plastic, may be poured into the mold so as to embed, in portions of first Frame 10 intended to be part of the Switch. The plastic insulates first frame 10 electrically once it is, by this method, secured in molded base 91. Once secured, first conducting strip 12 is embedded within base 91, while the portions of first frame 10 to be discarded 15 and 16 hang over, or extend from, the sides and ends of molded base 91.

FIG. 3 also shows two generally rectangular wells 110 and 111, formed in molded base 91, within which activation straps 40 and 41 may be seen. Activation straps 40 and 41, which may move freely within wells 110 and 111, may be crimped or bent along their length, as shown in FIG. 1, to provide variable activation pressures. FIG. 3 does not show activation openings, through which appropriate means may be inserted to apply pressure to activation straps 40 and 41 through molded base 91. Such activation openings, centered approximately on center landings 42 and 43, and which appear in FIG. 9, allow an operator to move activation straps 40 and 41 from the exterior of the Switch Cabinet by application of pressure by such appropriate means. FIG. 3 also shows first insulation displacement connector 30, and active electrode end tab 35. FIG. 3 also shows three insulation displacement connector channels 130, 131, and 132, into which contact leads (not shown) from a generator may be placed before Cabinet Top 90 is affixed to Cabinet Bottom (not shown).

Figure 4:
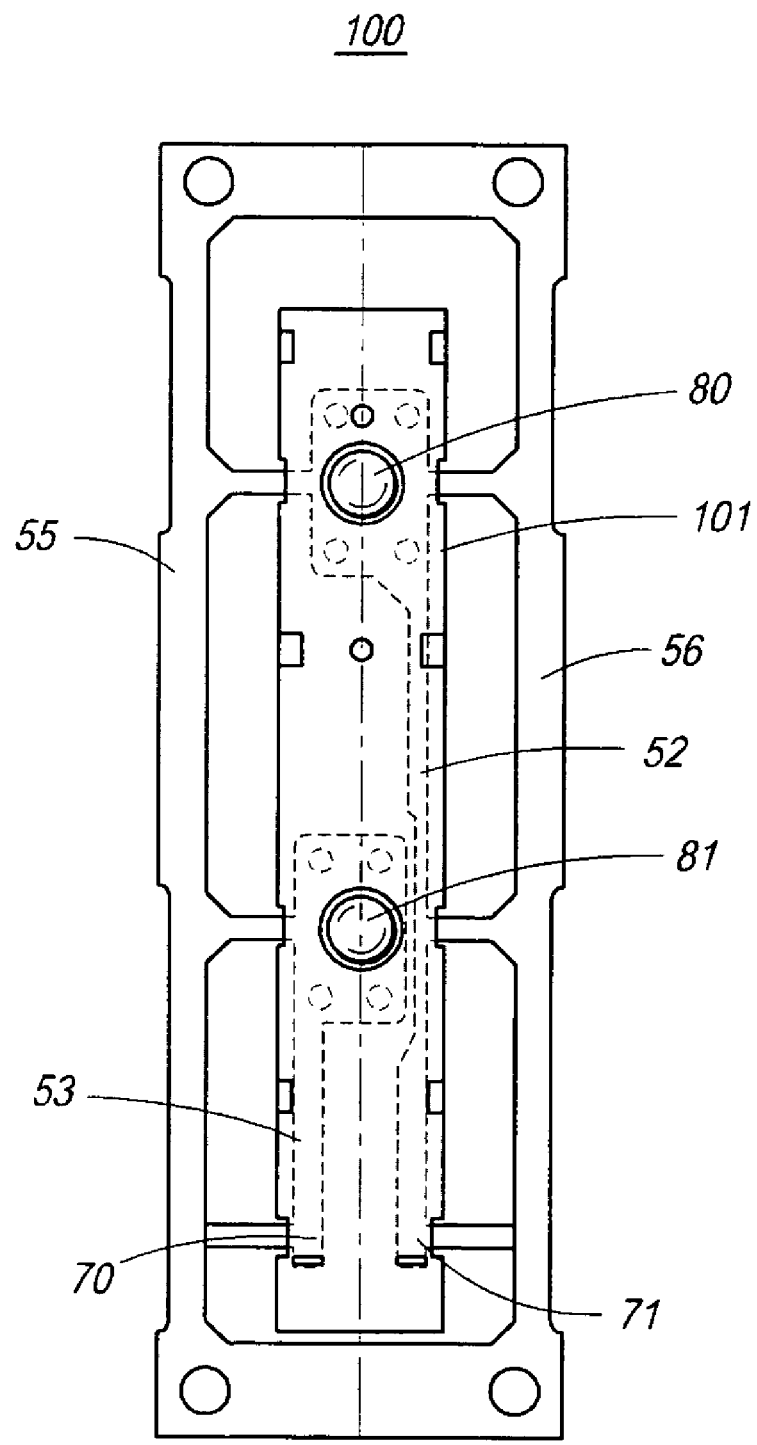
FIG. 4 is a plan view drawing of the second electrical circuit frame of FIG. 2, in which a Cabinet Bottom has been formed over the second frame by pouring of plastic into a second mold.

Turning now to FIG. 4, molded Cabinet bottom 100 of the Switch of the present invention is shown in top down, plan view, prior to cutting through Frame Isthmus 57, 58, 59, 60, 61, and 62 to separate (and discard) exterior portions 65 and 66 from Second Frame 50. The Cabinet Bottom molded base 101 (non-conductive exterior) is formed as a single piece, with conductive elements (the second frame 50 of FIG. 2) embedded within. Molded base 101 may be viewed as the second half of the full Switch Cabinet, with features of Second Frame 10 within molded based 101 presented in dotted lines. To form Cabinet Bottom 100, Second Frame 50 is positioned in a mold (not shown) intended to shape base 101 by molding plastic, non-conductive compound around Second Frame 50. Once in such position within such mold, suitable insulative material, generally plastic, may be poured into the mold so as to embed, in portions of Second Frame 50 intended to be part of the Switch. The plastic insulates Second Frame 50 electrically once it is, by this method, secured in molded base 101. Once secured, second conducting strip 52 and third conducting strip 53 are embedded within base 101, while the portions of second frame 50 to be discarded 55 and 56 hang over, or extend from, the sides and ends of base 101. FIG. 4 also shows second insulation displacement connector 70, third insulation displacement connector 71, and two dome contacts 80 and 81.

Figure 5:
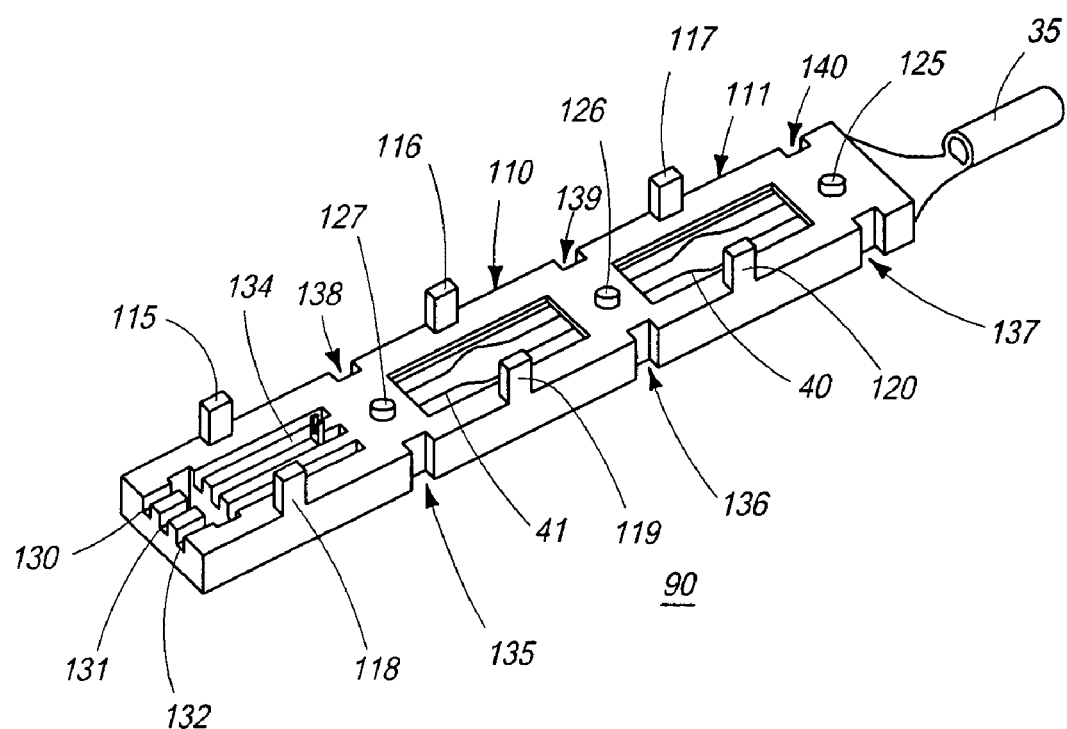
FIG. 5 is a perspective view drawing of the Cabinet Top of FIG. 3, with the first electrical circuit frame of FIG. 1 largely encased therein, in which the Cabinet Top containing the first frame has been separated from similar first frames in the reel of similar first frames.

FIG. 5 shows Cabinet Top 90 in perspective view, with its two generally rectangular well 110 and 111, within which activation straps 40 and 41 may be seen. FIG. 5 also shows Cabinet top assembly ribs 115, 116, 117, 118, 119, and 120. These assembly ribs are intended to facilitate one method of joining Cabinet Top 90 to Cabinet Bottom 100, as the assembly ribs slide into corresponding Bottom assembly channels (seen in FIG. 6) in the Cabinet Bottom 100. As second method of joining Cabinet Top 90 to Cabinet Bottom 100 is through insertion of Cabinet Top assembly pins 125, 126, and 127 into corresponding Cabinet Bottom assembly holes (seen in FIG. 6). Of course, either of these "snap fit" methods of joining Cabinet Top and Cabinet Bottom may be utilized to keep these two parts tightly joined, and thereby create the finished Cabinet, and the method better suited to full automation consists of using Cabinet Top assembly pins 125, 126, and 127 and corresponding Cabinet Bottom assembly holes.

FIG. 5 also shows Cabinet top assembly channels 135, 136, 137, 138, 139, and 140. These assembly channels are intended to facilitate one method of joining Cabinet Top 90 to Cabinet Bottom 100, as the assembly channels may allow corresponding Bottom assembly ribs (seen in FIG. 6) in the Cabinet Bottom 100 to slide together, and lock the Top and Bottom together. As noted above, this "snap fit" method of joining Cabinet Top and Cabinet Bottom may not be routinely used, as Cabinet Top assembly pins 125, 126, and 127 and corresponding Cabinet Bottom assembly holes are generally better suited to full automation.

FIG. 5 also shows three insulation displacement connector channels 130, 131, and 132, into which contact leads (not shown) from a generator may be placed before Cabinet Top 90 is affixed to Cabinet Bottom 100. FIG. 5 also shows the bent portion 134 of first insulation displacement connector 30 extending from Cabinet Top, so as to cut through insulation from such contact leads from the electrosurgical generator. Finally, FIG. 5 also shows crimped tubular end 35 of Switch metal First Frame 10.

As noted above in FIG. 3, wells 110 and 111 shown in FIG. 5 are formed in molded base 91, and allow activation straps 40 and 41 to move freely within wells 110 and 111, to provide variable activation pressures for the Switch. FIG. 3 does not show activation openings, through which appropriate means may be inserted to apply pressure to activation straps 40 and 41 through molded base 91. As noted above for FIG. 3, such activation openings are centered approximately on center landings 42 and 43, and allow an operator to move activation straps 40 and 41 from the exterior of the Switch Cabinet by application of pressure by appropriate means.

Figure 6:
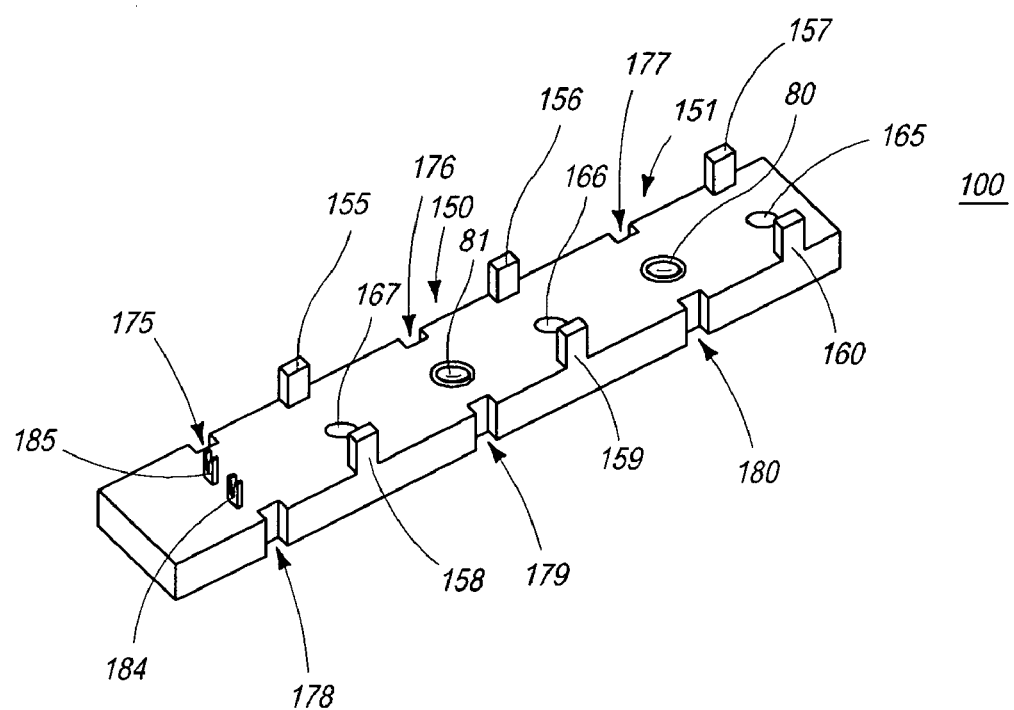
FIG. 6 is a perspective view drawing of the Cabinet Bottom of FIG. 4, with the second electrical circuit frame of FIG. 2 largely encased therein, in which the Cabinet Bottom containing the second frame has been separated from similar second frames in the re& of similar second frames.

FIG. 6 shows Cabinet Bottom 90 in perspective view, with its two generally circular openings 150 and 151, within which dome contacts 80 and 81 may be seen. FIG. 5 also shows Cabinet Bottom assembly ribs 155, 156, 157, 158, 159, and 160. These assembly ribs are intended to facilitate one method of joining Cabinet Top 90 to Cabinet Bottom 100, as the assembly ribs slide into corresponding Top assembly channels (seen in FIG. 5) in the Cabinet Top 90. FIG. 6 also shows Cabinet Bottom assembly channels 175, 176, 177, 178, 179, and 180. These assembly channels are intended to facilitate one method of joining Cabinet Top 90 to Cabinet Bottom 100, as the assembly channels may allow corresponding Top assembly ribs (seen in FIG. 5) in the Cabinet Top 90 to slide together, and lock the Top and Bottom together. As noted above, this "snap fit" method of joining Cabinet Top and Cabinet Bottom may not be routinely used, as Cabinet Top assembly pins 125, 126, and 127 and corresponding Cabinet Bottom assembly holes 165, 166, and 167, as a second method of joining Cabinet Top 90 to Cabinet Bottom 100, is generally better suited to full automation. FIG. 6 also shows the bent portion 184 of second insulation displacement connector 70, and the bent portion 185 of third insulation displacement connector 71, each extending from Cabinet Bottom, so as to cut through insulation from contact leads from the electrosurgical generator.

Figure 7:
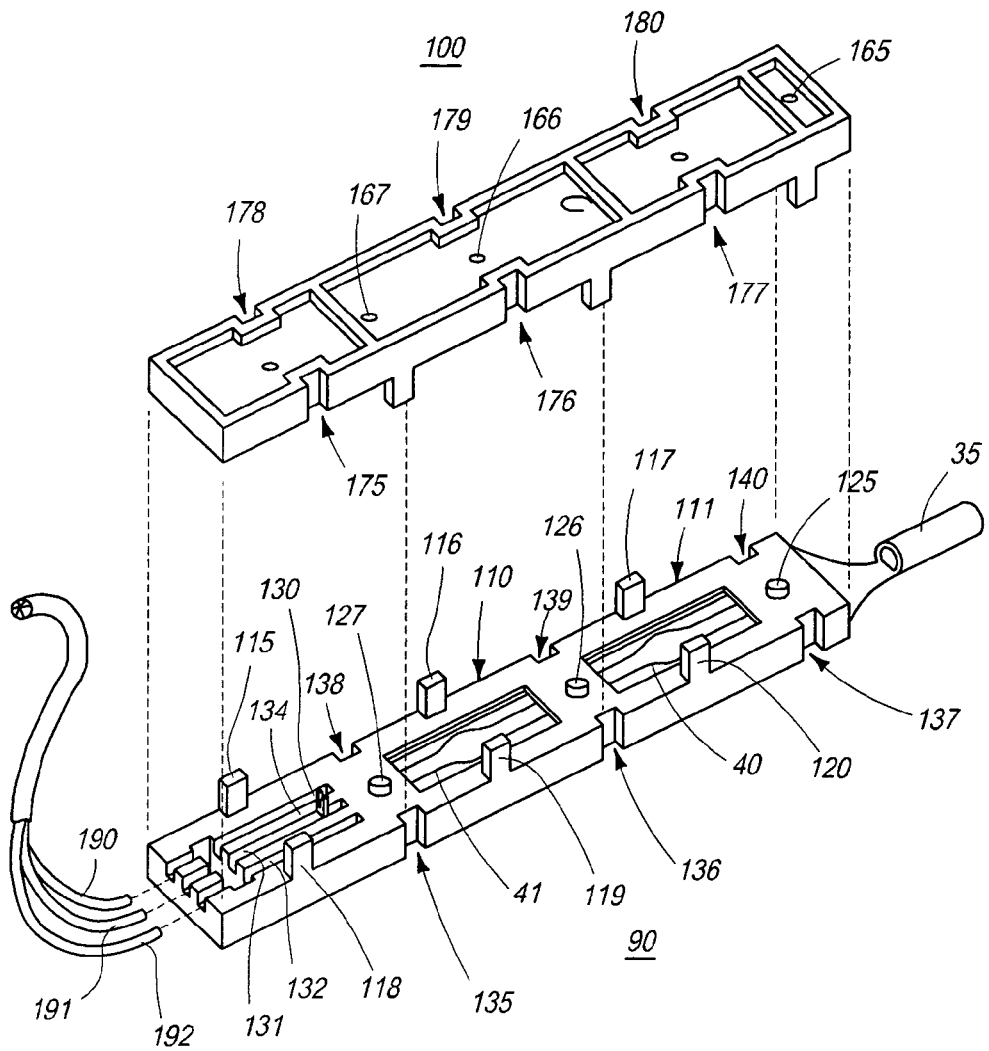
FIG. 7 is a perspective view drawing of the Cabinet Top of FIG. 5 positioned above the Cabinet Bottom of FIG. 6 prior to joining Cabinet Top and Cabinet Bottom.

In FIG. 7, Cabinet Top 90 and Cabinet Bottom 100 are again shown in perspective view, positioned so as to show how they will be joined, the Bottom 100 turned over so that such joinder may be effected. Here we may see Top assembly ribs 115, 116, 117, 118, 119, and 120 about to engage and slide into corresponding Bottom assembly channels 175, 176, 177, 178, 179, and 180, and Bottom assembly ribs 155, 156, 157, 158, 159, and 160 about to engage and slide into corresponding Top assembly channels 135, 136, 137, 138, 139, and 140, to thereby lock Top 90 and Bottom 100 together. As noted above, the second and preferred method of joining Cabinet Top 90 to Cabinet Bottom 100 is through insertion of Cabinet Top assembly pins 125, 126, and 127 into Cabinet Bottom assembly holes 165, 166, and 167. FIG. 7 also shows two generally rectangular wells 110 and 111, within which activation straps 40 and 41 may be seen. FIG. 7 also shows three insulation displacement connector channels 130, 131, and 132, into which contact leads 190, 191, and 192 from a generator may be placed before Cabinet Top 90 is affixed to Cabinet Bottom 100. Upon such affixation, bent portion 134 of first insulation displacement connector 30 extending from Cabinet Top molded base 91, bent portion 184 of second insulation displacement connector 70 extending from Cabinet Bottom molded base 101, and bent portion 185 of third insulation displacement connector 71 extending from Cabinet Bottom molded base 101, cut through insulation from contact leads 190, 191, and 192 from the electrosurgical generator. Finally, FIG. 7 also shows crimped tubular end 35 of Switch metal First Frame 10.

Figure 8:
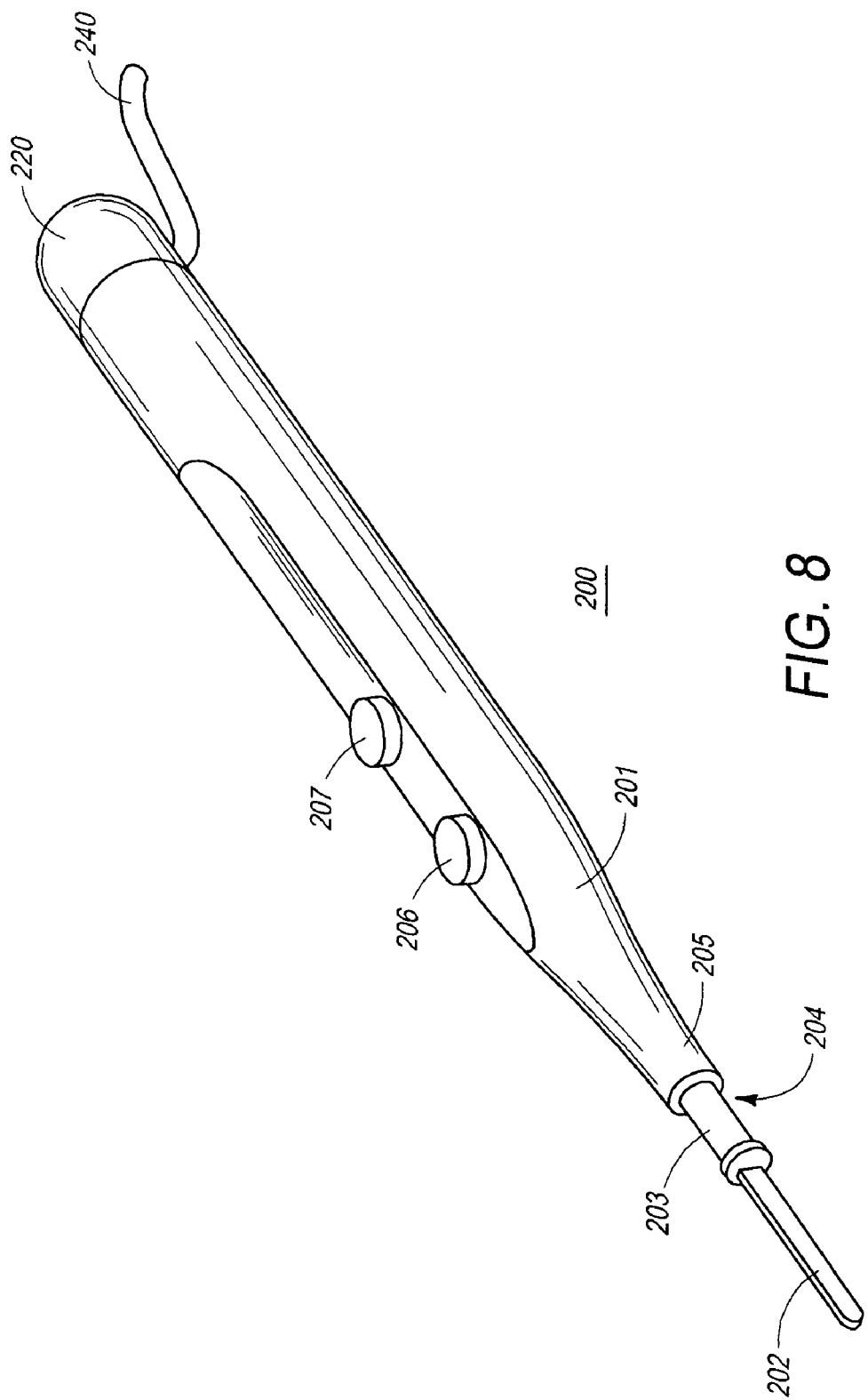
FIG. 8 is a perspective view drawing of the first preferred embodiment of the Pencil of the present invention in its completed configuration, along with a portion of the conductors by which the Pencil is connected to an electrical generator.

Referring to FIG. 8, a first preferred embodiment of the Pencil of the present invention in its completed configuration is shown in perspective view, along with a portion of the conductors by which the Pencil is connected to an electrical generator. In FIG. 8, Pencil 200 is comprised of a unitary Housing 201 formed generally by injection molding using a suitable plastic material. Active electrode 202, which acts as a cutting blade, is formed with non-conductive, and insulative, plastic "over mold" electrode holder 203, which allows a user to safely remove active electrode 202 from Housing 201, and isolate heat generated by active electrode 202. Electrode holder 203, in turn, may be inserted into Housing front end aperture 204 at the corresponding "front" end 205 of Housing 201, which aperture 204 is formed to snugly receive electrode holder 203. Active electrode 202 generally extends through electrode holder 203, and into Housing 201, to reach crimped tubular end of Switch metal frame extending from the "front" of the Switch Cabinet (not shown in FIG. 1), once electrode holder 203 is inserted into aperture 204. Active electrode 202 may be finally positioned as shown in FIG. 8 during manufacture of Pencil 200, or thereafter by a user wishing to change active electrode blades. External activation Buttons 206 and 207 are shown, along with closure Cap 220 and a portion of cable conductors 240 by which Pencil 200 is connected electrically to a generator (not shown).

Figure 9:
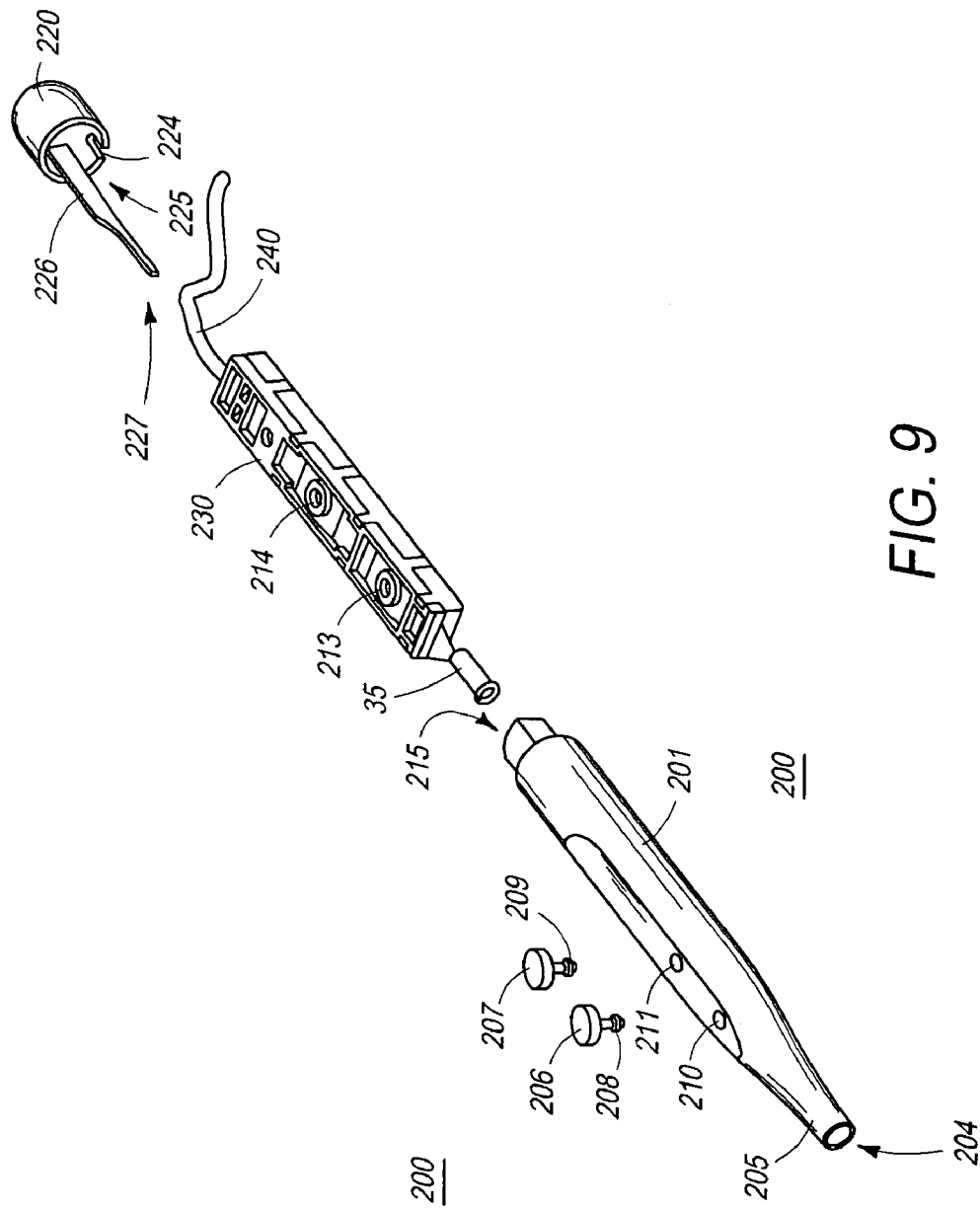
FIG. 9 is a exploded perspective view drawing of the Pencil shown in FIG. 8, viewed from the top front quarter of the Pencil, after the Cabinet Top has been joined to the Cabinet Bottom.

Now referring to FIG. 9, Pencil 200 is shown in exploded view, with each component shown in FIG. 8 ready for assembly by fully automated machinery. Accordingly, Pencil 200 unitary Housing 201 is ready for joining with active electrode 202, which is already "over molded" with electrode holder 203, and positioned near front end aperture 204 at front end 205 of Housing 201. In this embodiment, electrode holder 203 merely holds active electrode 202 within aperture 204, so that active electrode 202 may connect electrically to the crimped tubular end 35 of Switch metal First Frame 10. External activation Buttons 206 and 207 are again shown, with Button stems 208 and 209, before Button stems 208 and 209 are inserted into Housing openings 210 and 211.

In FIG. 9, Cabinet 230 is shown, with Cabinet activation openings 213 and 214 in the top of Cabinet 230. Stems 208 and 209 of Buttons 206 and 207, prior to insertion into Housing openings 210 and 211, are also shown in FIG. 9, as is a portion of generator conductors 240 by which Pencil 200 is connected electrically to a generator (not shown). Housing openings 210 and 211 are positioned over corresponding Cabinet activation openings 213 and 214 formed in the top of Cabinet 230 once Cabinet 230 is positioned within Housing 201 through back end aperture 215, and pressed into place in Housing 201. Accordingly, stems 208 and 209 of the Buttons 206 and 207, when they are properly positioned and pressed into place, will extend to a position directly over or touching the center landings 42 and 43 (not shown in FIG. 9) of activation straps 40 and 41 (not shown in FIG. 9) within Cabinet 230. Cabinet 201, within which the Switch Cabinet 230 resides, is also shown in FIG. 9, along with crimped tubular end 35 as the extension of Switch metal first frame extending from front of Switch Cabinet 230, and tubular end 35 is ready for insertion into back end aperture 215 of Housing 201.

Closure Cap 220 is again shown in FIG. 9, however, some of the interior features of Cap 220 may be seen in this exploded view of Pencil 200. In particular Cap 220 is formed with Cap slit 224, which matches positionally, and coacts with, a corresponding Housing slit (not shown in FIG. 9). Cap slit 224, in this embodiment, is formed near open end 225 of Cap 220, and so as to end up on the bottom side of Housing 201 once Pencil 200 is assembled. Finally, Cap push pin 226, formed so as to end up on the top side of Housing 201, is shown. Push pin 226 is also formed with a taper toward push pin end 227, which taper allows easier, and automated, closure of Pencil 200 as Cap 220 is positioned over aperture 215, and snapped into place to close Pencil 200. When assembled according to FIG. 9, crimped tubular end 35 of Switch metal first frame 10 extends from Cabinet 230 toward the workpiece when the Cabinet 230 is in final position within Housing 201. Crimped tubular end 35 of the Switch metal first frame 10 is also formed to fit snugly within an interior portion of front end aperture 204, while electrode holder 203 fits snugly within the opening of front end aperture 204. The fit of tubular end 35 and electrode holder 203 within front end aperture 204 reduces transmission of moisture to the interior of Pencil 200 when in use. Yet tubular end 35 and electrode holder 203 are also formed to slide easily into their respective positions within front end aperture 204, so crimped tubular end 35 is not bent during assembly of Pencil 200, and replacement of active electrode 202, within electrode holder 203, by a user is simple and quick.

Figure 10:
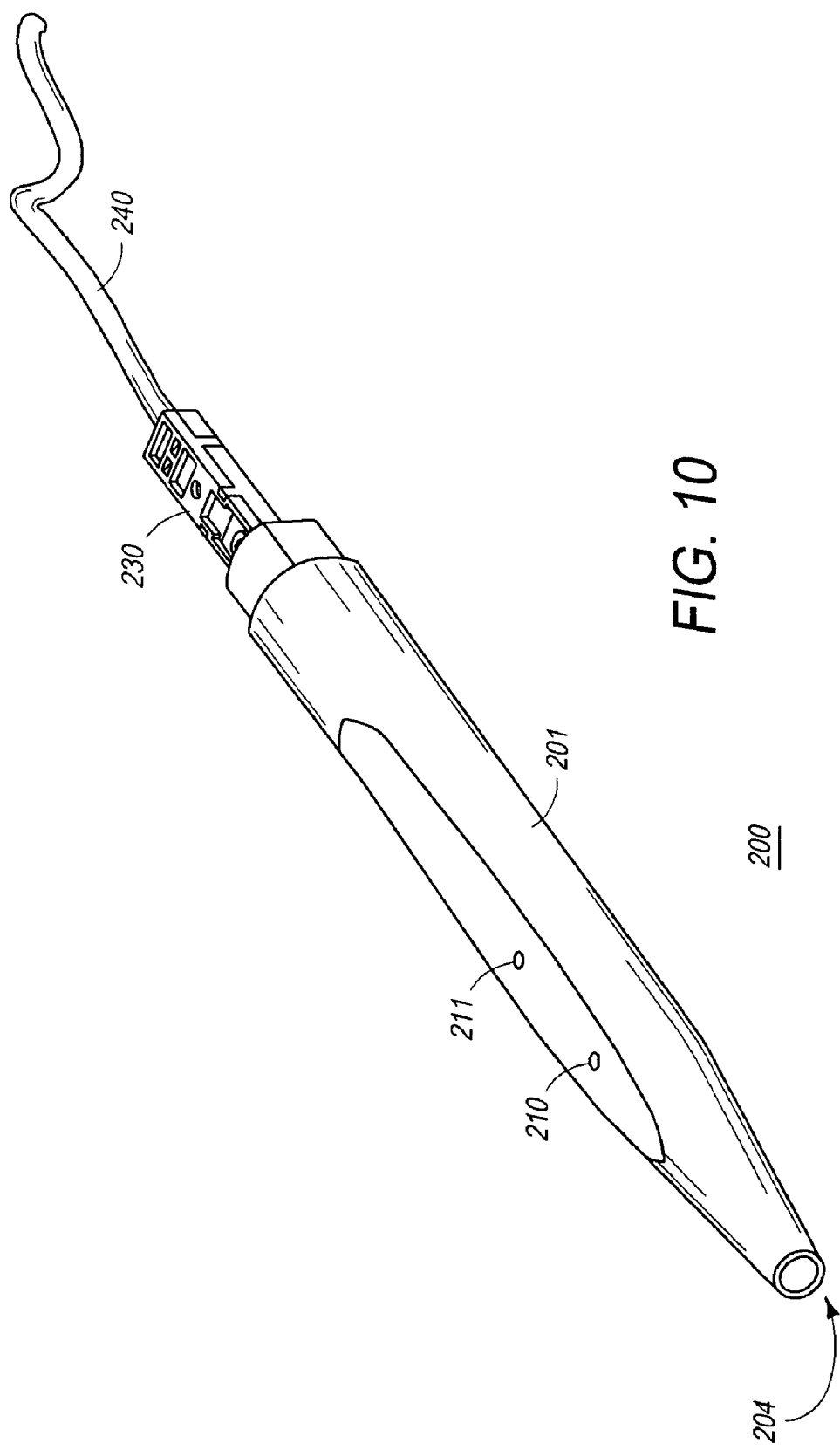
FIG. 10 is a perspective view drawing of the Housing of the Pencil shown in FIG. 9, in which the Switch of the present invention is being inserted into the back end aperture of the Housing.

Turning now to FIG. 10, Pencil 200 unitary Housing 201 is being joined with Cabinet 230, with pre-attached generator conductors 240. Housing openings 210 and 211 for Button stems (not shown) may also be seen, along with front end aperture 204. The simplicity of these components allow each piece to be independently grasped by automated machinery, oriented correctly for assembly, joined to one another, and pressed into place. All remaining components are similarly simple, easy and inexpensive to manufacture, and subject to fully automated assembly. Accordingly, from the view of Pencil 200 depicted in FIGS. 8 and 9, each piece of Pencil 200 may be, in order, joined to Housing 201, and pressed into place.

Turning to FIG. 11, the back end of Housing 201 is shown, with back end aperture 215, into which Switch Cabinet (not shown) may be placed, apparent. Lip 252 of back end aperture 215 appears in detail, with undercut area 250 of Housing 201 ready for engagement with open end of Cap (not shown) for closure of Housing 201. Interior walls 251 of Housing 201, toward back end aperture 215, are differentially widened in this embodiment, to allow easy, fully automated, insertion of Cabinet (not shown) within Housing 201 during assembly. In addition, ramps 255, 256, 257, and 258, formed within interior of Housing 201, beginning at or nearer back end aperture 215, are formed on top and bottom interior surfaces 259 and 260 of Housing 201. Ramps 255, 256, 257, and 258 are generally lower in aspect near back end aperture 215, and they increase in height or depth as they approach front end 205 of Housing 201. Accordingly, the Switch Cabinet may be inserted into back end aperture 215 of Housing 201, and slid into Housing 201, the interior of which may narrow toward front end 205 of Housing 201, while ramps 255, 256, 257, and 258 within interior section 251 close around the Cabinet snugly, to keep it firmly positioned within Housing 201. At the end of its travel within Housing 201, the Cabinet may bear against Housing stop (not shown), and crimped tubular end 35 of extension of Switch metal first frame 10 may reside snugly within, Housing 201 front end aperture 204. Housing slit 60 appears on the bottom side of lip 252 of back end aperture 215.

A foreshortened view of the front end interior of Housing 201 is shown in FIG. 12. Foreshortening this view of this section of the interior of Housing 201 allows us to see details at the front end interior of Housing 201. In FIG. 4, we can see a portion of interior walls 251 of Housing 201, near stop 271, is formed to receive the Cabinet. As the interior of this section of Housing 201 is just larger than the Cabinet, this section of Housing 201 may firmly hold the Cabinet within Housing 201, without material gap between the Cabinet and Housing 201 interior, which gap might allow vibration, or "play," between these components. The Cabinet may be formed with small protrusions (not shown) which may bear against one or more of the interior walls 251 of Housing 201 once the Cabinet is inserted into Housing 201. Such protrusions may be deformed as the Cabinet is pressed into position against stop 271, and held firmly within Housing 201 by the narrowness of interior walls 251 and one or more of the heightened ends of ramps 255, 256, 257, and 258 near stop 271. In the alternative, protrusions (not shown) may be formed on one or more interior surfaces of Housing 201, and a standard Cabinet (i.e., without protrusions) used. The protrusions, whether formed on the Cabinet or on the interior walls 251 of Housing 201, provide a "compression fit" of Switch Cabinet within Housing 201 after the Cabinet is pressed into final position within Housing 201, and against stop 271, during assembly. At the end of its travel within Housing 201, crimped tubular end 35 of extension 12 of Switch metal first frame resides snugly within Housing 201 front end aperture 204.

In FIG. 12, the front end interior of Housing 201 is formed with a "stop" 271 or "seat," up against which the Cabinet is pressed during assembly, and against which the Cabinet is seated after Cap (not shown in FIG. 12) is fitted over back end aperture 215 of Housing 201 to close Housing 201 over the Cabinet. Stop 271 is generally formed within Housing 201 to allow the Cabinet to slide forward in Housing 201 during assembly, sufficiently far to allow crimped tubular end 35 of Switch metal first frame 12 to extend into front end aperture 204 of Housing 201. The Cabinet, within which the Pencil Switch resides, and stop 271, are each formed to closely engage one another, and the Cabinet edges and stop 271 corners may each be rounded by adding a radius, or increasing the existing radius, to reduce strain and insure proper seating of the Cabinet against stop 271 within Housing 201. Housing slit 224, formed to allow access to the interior of Housing 201 by generator conductors 240, again appears on the bottom side of lip 252 of back end aperture 215.

Continuing with the assembly process, FIG. 13 shows Pencil 200 partially assembled in rear quarter perspective cut away view. In FIG. 13, Switch Cabinet 230 has been fully inserted into Housing 201, so that the forward end of Cabinet 230 bears against stop 271 within the interior of the forward end of Housing 201. In this position, Cabinet 230 determines the positions of crimped tubular end and extension of Switch metal frame (neither component shown here) firmly and snugly inserted into, and held within, the back portion of front end aperture 204. Cabinet 230 is retained in this position by Cap 220, and more particularly by Cap push pin 226, with its tapered push pin end 227, which is in length long enough to extend from the back end of Cap 220 to the back end of Cabinet 230 once Cabinet 230 is positioned against stop 271 in Housing 201. Housing openings 210 and 211 may also be seen in FIG. 13, as may the end of generator conductors 240 attached to Cabinet 230 at their point of insertion 275 into Cabinet 230 for connection to Switch metal frame by insulation displacement connectors 276.

Continuing with the assembly process, FIG. 14 shows Pencil 200 fully assembled in cross section. In FIG. 14, Switch Cabinet 230 has again been fully inserted into Housing 201, so that the forward end of Cabinet 230 bears against stop 271 within forward end of Housing 201. Crimped tubular end 35 and extension of Switch metal first frame 10 are each shown here firmly and snugly inserted into the back portion of front end aperture 204, and held within aperture 204 by Cabinet 230, which is in turn retained in position by Cap 220 and push pin 226, with its tapered push pin end 227. Again, push pin 226 and tapered push pin end 227 are in length long enough to extend from the back end of Cap 220 to the back end of Cabinet 230 once the Cabinet is positioned against stop 271 in Housing 201. Housing openings 220 and 221 may also be seen in FIG. 14, into which stems 208 and 209 of Buttons 206 and 207 have been inserted. Stems 208 and 209 also extend through activation openings activation openings 213 and 214 in the top of Cabinet 230. Active electrode 202 may be seen in FIG. 14 inserted into, and extending through, electrode holder 203, within front end aperture 204 at front end 205 of Housing 201. In this embodiment, electrode holder 203 is a non-conductive, and insulative, plastic "over mold" extender used to hold active electrode 202, and connect it electrically to the crimped tubular end 35 and extension of Switch metal first frame 12. As in FIG. 13, the end of generator conductors 240 may be seen, attached to Cabinet 230 at their point of insertion 275 into Cabinet 230, and Cap 220 has been fitted over back end aperture 215 of Housing 201 to close Housing 201 over Cabinet 230.

FIG. 15 shows details of joinder of Cap 220 and Housing 201, in which Cap groove 280 (in this embodiment) and Housing ridge 281 are engaged and "snapped" into place. Circumferential groove 280 and matching circumferential ridge 281 generally extend around the circumference of Cap 220 and Housing 201, for positive locking action between these components, however single or multiple bumps, with matching pits (not shown), may also be used to lock Cap 220 to Housing 201. Groove 280 and matching ridge 281 are generally also formed to lock into place at undercut area 250 of Housing 201, so that at least one face 285 at Cap opening 241 is generally tightly seated against a corresponding face 286 formed by the undercut at or near back end aperture 215 of Housing 201, thereby smoothly (and tightly) closing Cap 220 to Housing 201. Cap push pin 224 is, for clarity, not shown in FIG. 15, however the preferred embodiment includes Cap push pin as an assist to slide Cabinet 230 into position against stop 271 during assembly, and hold it against stop 271 during use of Pencil 200. In FIG. 15, Housing slit 60 is formed on the bottom side of lip 252 of back end aperture 215, to allow access to the interior of Housing 201 by generator conductors 240. Cap slit 240 also appears in this embodiment, formed near open end 241 of Cap 220, so as to end up on the bottom side of Housing 201 once Pencil 200 is assembled, and formed opposite Housing slit 260 to provide additional clearance for passage of generator conductors 240 from generator (not shown) to the interior of Housing 201.

Second Preferred Embodiment

Figure 16:
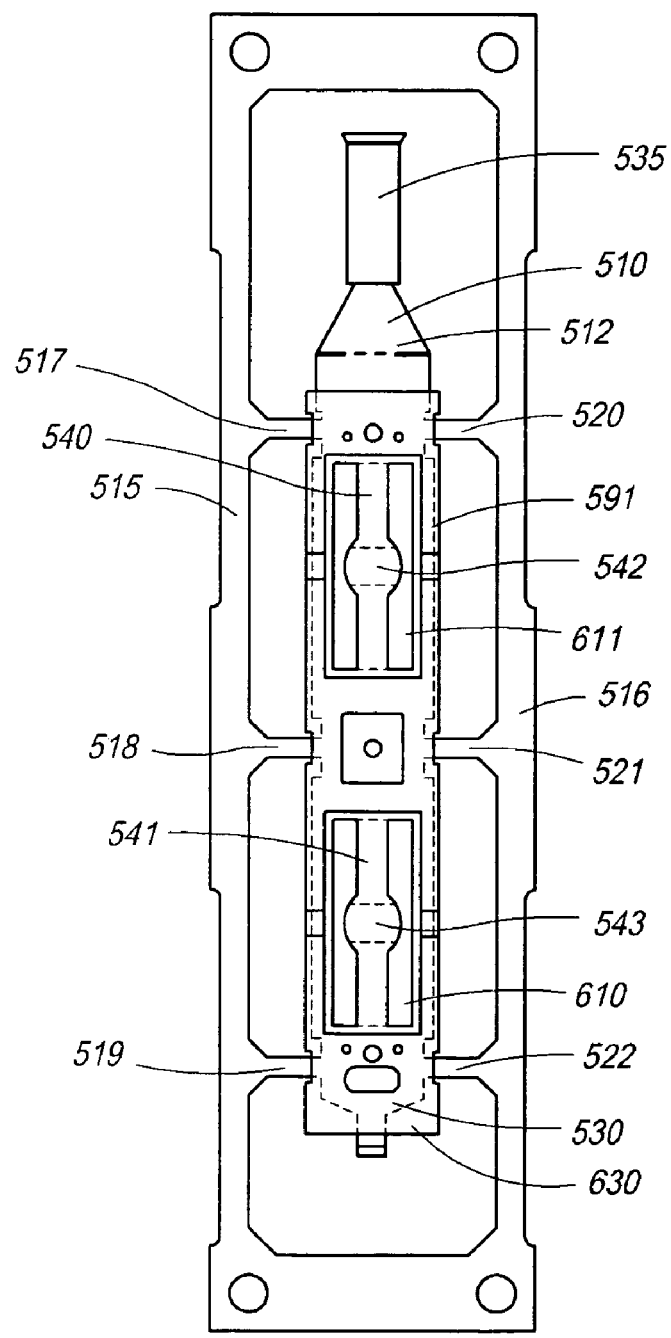
FIG. 16 is a plan view drawing of a first electrical circuit frame, for a second preferred embodiment of the Switch of the present invention, viewed from the top of the frame, in which a Cabinet Top has been formed over the first frame by pouring of plastic into a first mold, so the first frame is largely encased within the Cabinet Top, and the Cabinet Top has been separated from similar first frames in the reel of similar first frames.

Turning now to FIG. 16, a second embodiment of an electrical circuit First Frame and molded Cabinet Top 590 of the Switch of the present invention is shown. In this second embodiment a First Frame 590 is, like the First Frame 10 of the first embodiment (FIG. 1), comprised of a unitary piece, formed from a blank sheet of conductive metal by stamping. Again, First Frame 590 may be formed from a single sheet, or a reel of electrically conductive material as shown in FIG. 1, and explained in the text which accompanies FIG. 1. FIG. 16 shows the molded Cabinet Top 590 of the Switch of the present invention in bottom up, plan view. Specifically, molded Cabinet Top 590 is shown prior to cutting through Frame Isthmus 517, 518, 519, 520, 521, and 522 to separate (and discard) exterior portions 515 and 516 from First frame 510. The Cabinet top molded base 591 (non-conductive exterior) is formed as a single piece, with conductive elements (the metal frame 510 of FIG. 16) embedded within. Molded base 591 may be viewed as one half of the full Switch Cabinet, with features of First Frame 510 within molded base 591 presented in dotted lines. To form Cabinet top 590, First Frame 510 is positioned in a mold (not shown) intended to shape base 591 by molding plastic, non-conductive compound around First Frame 510. Once in such position within such mold, suitable insulative material, generally plastic, may be poured into the mold so as to embed, portions of First Frame 510 intended to be part of the Switch. The plastic insulates First Frame 510 electrically once it is, by this method, secured in molded base 591. Once secured, first conducting strip 512 is embedded within base 591, while the portions of first frame 510 to be discarded 515 and 516 hang over, or extend from, the sides and ends of molded base 591.

FIG. 16 also shows two generally rectangular wells 610 and 611, formed in molded base 591, within which activation straps 540 and 541 may be seen. Activation straps 540 and 541, which may move freely within wells 610 and 611, may be crimped or bent along their length, as shown in FIG. 16, to provide variable activation pressures. FIG. 16 does not show activation openings in molded base 591, through which appropriate means may be inserted to apply pressure to activation straps 540 and 541 through molded base 591. Such activation openings, centered approximately on center landings 542 and 543, allow an operator to move activation straps 540 and 541 from the exterior of the Switch Cabinet by application of pressure by such appropriate means. FIG. 16 also shows first insulation displacement connector 530, and active electrode end tab 535.

We may begin to appreciate the differences between First Frame 510 within molded base 591 of this second embodiment, and the First Frame 10 within molded base 91 of the first embodiment referring to FIG. 16, and particularly with reference to the proximal end 630 of molded base 591. Here we can see no three insulation displacement connector channels similar to the insulation displacement connector channels 130, 131, and 132 of the first embodiment (see FIG. 3 and FIG. 5). Instead of insulation displacement connector channels, into which contact leads from a generator may be placed, in order to connect the Cabinet of the second embodiment to such generator, proximal end 630 of molded base 591 is shortened. The Cabinet of the second embodiment is therefore shorter, which allows a shorted Pencil overall. The Cabinet of the second embodiment of the present invention is electrically connected to a generator by alternate means, which will become apparent in drawings which follow.

Figure 17:
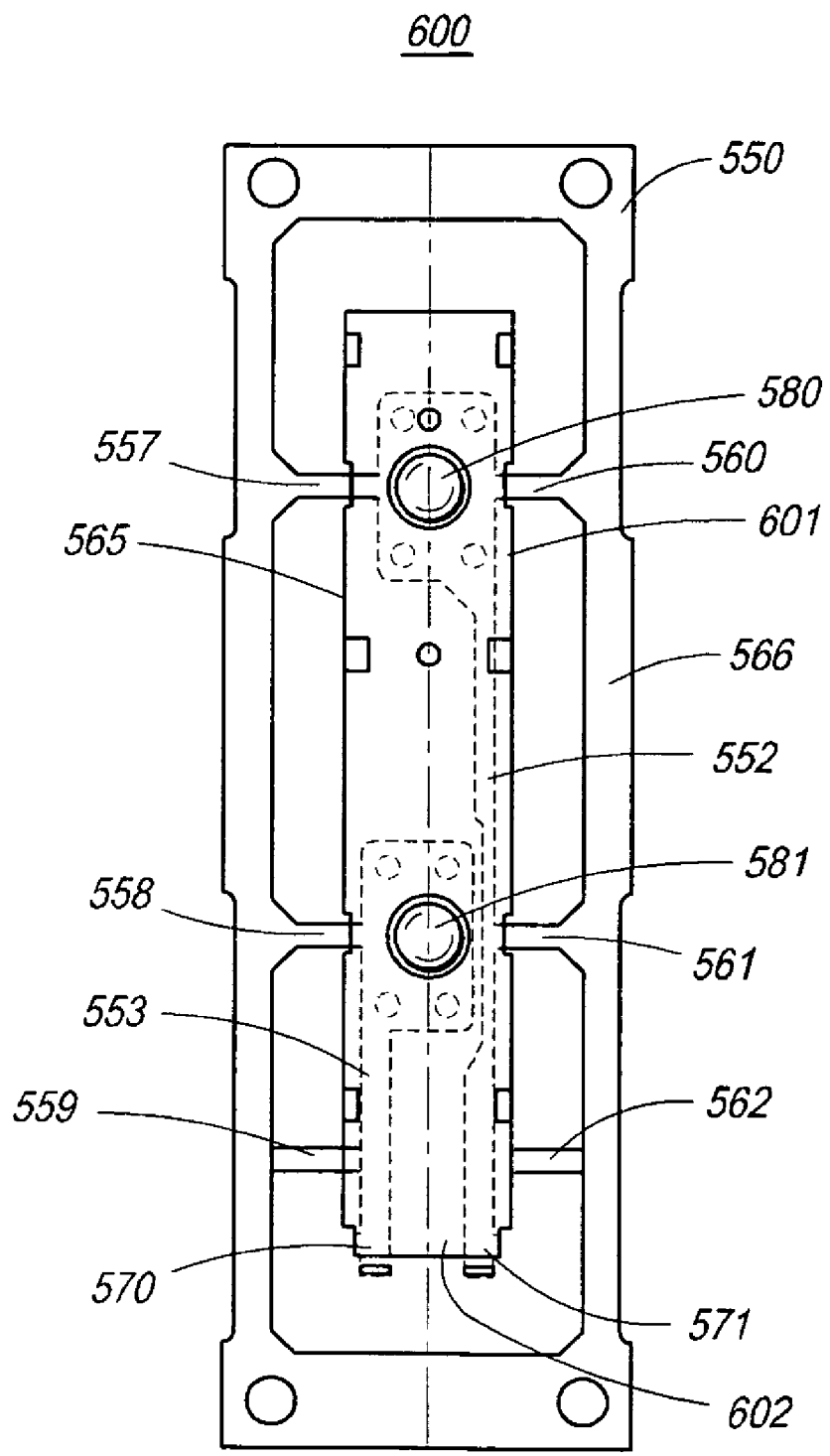
FIG. 17 is a plan view drawing of a second electrical circuit frame, for the second preferred embodiment of the Switch of the present invention, again viewed from the top of the frame, in which a Cabinet Bottom has been formed over the second frame by pouring of plastic into a second mold, so the second frame is largely encased within the Cabinet Bottom, and the Cabinet Bottom has been separated from similar second frames in the reel of similar second frames.

Turning now to FIG. 17, a second embodiment of a combined electrical circuit Second Frame in molded Cabinet Bottom 600 of the Switch of the present invention is shown. In this second embodiment Second Frame 600 is, like the Second Frame 50 of the first embodiment (FIG. 2), comprised of a unitary piece, formed from a blank sheet of conductive metal by stamping. Again, First Frame 600 may be formed from a single sheet, or a reel of electrically conductive material as shown in FIG. 2, and explained in the text which accompanies FIG. 2. Molded Cabinet bottom 601 of the Switch of the present invention is shown in top down, plan view, prior to cutting through Frame Isthmus 557, 558, 559, 560, 561, and 562 to separate (and discard) exterior portions 565 and 566 from Second Frame 550. The Cabinet Bottom molded base 601 (non-conductive exterior) is formed as a single piece, with conductive elements (the second frame 550 of FIG. 17) embedded within. Molded base 601 may be viewed as the second half of the full Switch Cabinet, with features of Second Frame within molded based 601 presented in dotted lines. To form Cabinet Bottom 600, Second Frame 550 is positioned in a mold (not shown) intended to shape base 601 by molding plastic, non-conductive compound around Second Frame 550. Once in such position within such mold, suitable insulative material, generally plastic, may be poured into the mold so as to embed, in portions of Second Frame 550 intended to be part of the Switch. The plastic insulates Second Frame 550 electrically once it is, by this method, secured in molded base 601. Once secured, second conducting strip 552 and third conducting strip 553 are embedded within base 601, while the portions of second frame 550 to be discarded 565 and 566 hang over, or extend from, the sides and ends of base 601. FIG. 17 also shows second insulation displacement connector 570, third insulation displacement connector 571, and two dome contacts 580 and 581.

We may again begin to appreciate the differences between Second Frame 600 within molded base 601 of this second embodiment, and the Second Frame 100 within molded base 101 of the first embodiment by referring to FIG. 17, and particularly with reference to the proximal end 602 of molded base 601. Here we can see a shortened proximal end 602 of molded base 601, which shortening corresponds to the shortening of proximal end 630 of molded base 591 of molded Cabinet Top 590. The Cabinet of the second embodiment is therefore shorter, which allows a shorted Pencil overall. The Cabinet of the second embodiment of the present invention is electrically connected to a generator by alternate means, which will become apparent in drawings which follow.

Cabinet Top 590, with its two generally rectangular wells 610 and 611, and Cabinet Bottom 600, with its second insulation displacement connector 570, third insulation displacement connector 571, and two dome contacts 580 and 581, may be joined by assembly ribs and corresponding assembly channels, or by assembly pins and corresponding assembly holes. Using either method, the Top and Bottom may be locked together as they are joined to "snap fit." Once joined, Cabinet Top 590 and Cabinet Bottom 600, center landings 542 and 543 of activation straps 540 and 541 may be moved within wells 610 and 611, from the exterior of the Switch Cabinet by application of pressure by appropriate means through activation openings (not shown), which are centered approximately on center landings 542 and 543. With such activation, activation straps 540 and 541 may be bent sufficiently to create electrical contact between center landings 542 and 543 of Cabinet Top 590 and dome contacts 580 and 581 of Cabinet Bottom 600.

Figure 18:
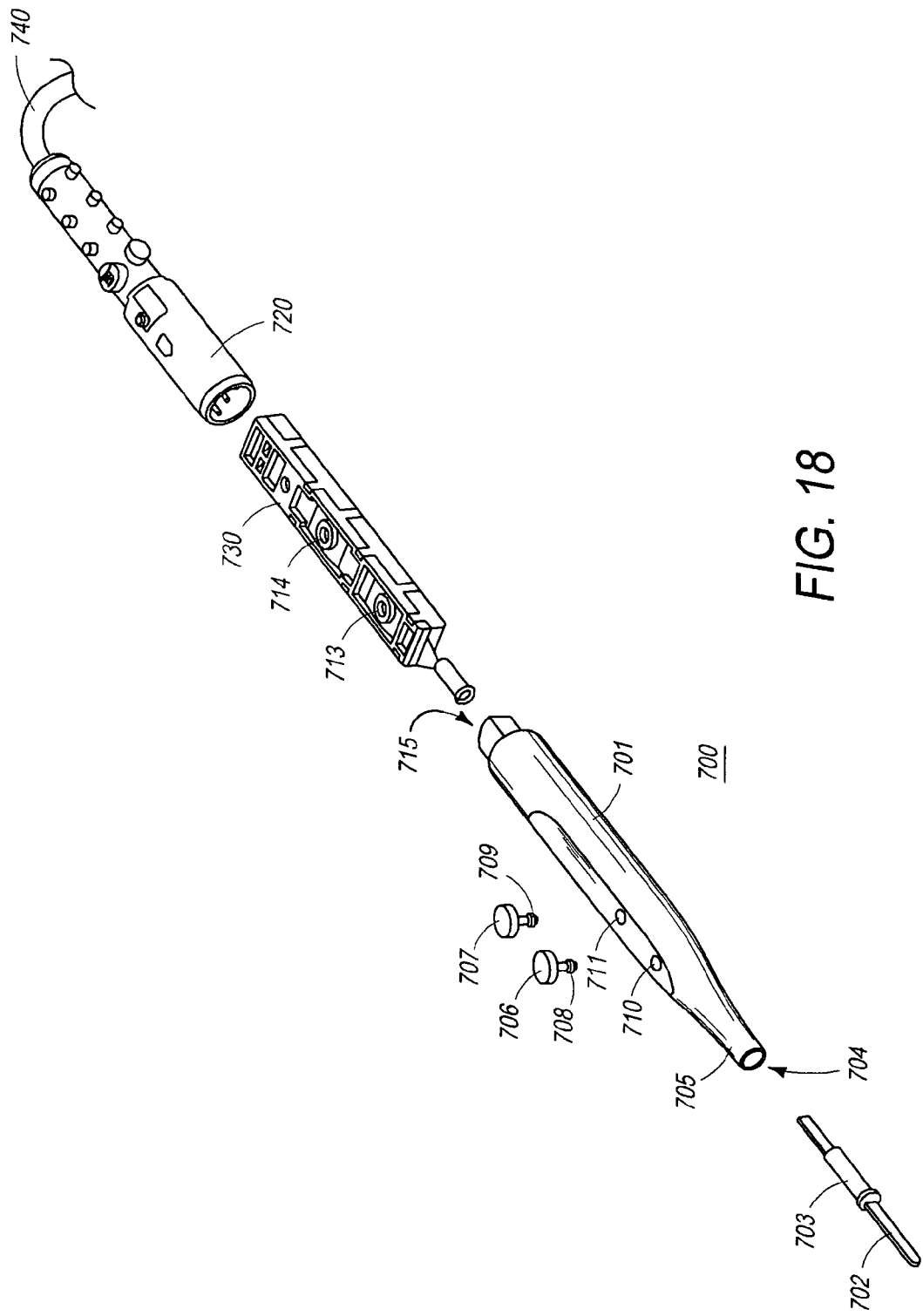
FIG. 18 is a exploded perspective view drawing of a second preferred embodiment of the Pencil of the present invention, viewed from the top front quarter of the Pencil, after the Cabinet Top of FIG. 16 has been joined to the Cabinet Bottom of FIG. 17 to create the second preferred embodiment of the Switch of the present invention.

Referring to FIG. 18, Pencil 700 is shown in exploded view, with each component shown ready for assembly by fully automated machinery. Accordingly, Pencil 700 unitary Housing 701 is ready for joining with active electrode 702, which is already "over molded" with electrode holder 703, and positioned near front end aperture 704 at front end 705 of Housing 701. In this embodiment, electrode holder 703 merely holds active electrode 702 within aperture 704, so that active electrode 702 may connect electrically to the crimped tubular end 535 of Switch metal First Frame 510. External activation Buttons 706 and 707 are again shown, with Button stems 708 and 709, before Button stems 708 and 709 are inserted into Housing openings 710 and 711.

In FIG. 18, Cabinet 730 is shown, with Cabinet activation openings 713 and 714 in the top of Cabinet 730. Stems 708 and 709 of Buttons 706 and 707, prior to insertion into Housing openings 710 and 711, are also shown in FIG. 18, as is the Cap 720 is of the "Cap and Cable Assembly," and a portion of generator conductors 740 by which Pencil 700 is connected electrically to a generator (not shown). Housing openings 710 and 711 are positioned over corresponding Cabinet activation openings 713 and 714 formed in the top of Cabinet 730 once Cabinet 730 is positioned within Housing 701 through back end aperture 715, and pressed into place in Housing 701. Accordingly, stems 708 and 709 of the Buttons 706 and 707, when they are properly positioned and pressed into place, will extend to a position directly over or touching the center landings 542 and 543 (not shown in FIG. 18) of activation straps 540 and 541 (not shown in FIG. 18) within Cabinet 730. Cabinet 701, within which the Switch Cabinet 730 resides, is also shown in FIG. 18, along with crimped tubular end 535 as the extension of Switch metal first frame extending from front of Switch Cabinet 730, and tubular end 535 is ready for insertion into back end aperture 715 of Housing 701. The function and operation of the Cap and Cable Assembly are explained more fully in connection with FIG. 24 and FIG. 25.

Figure 19:
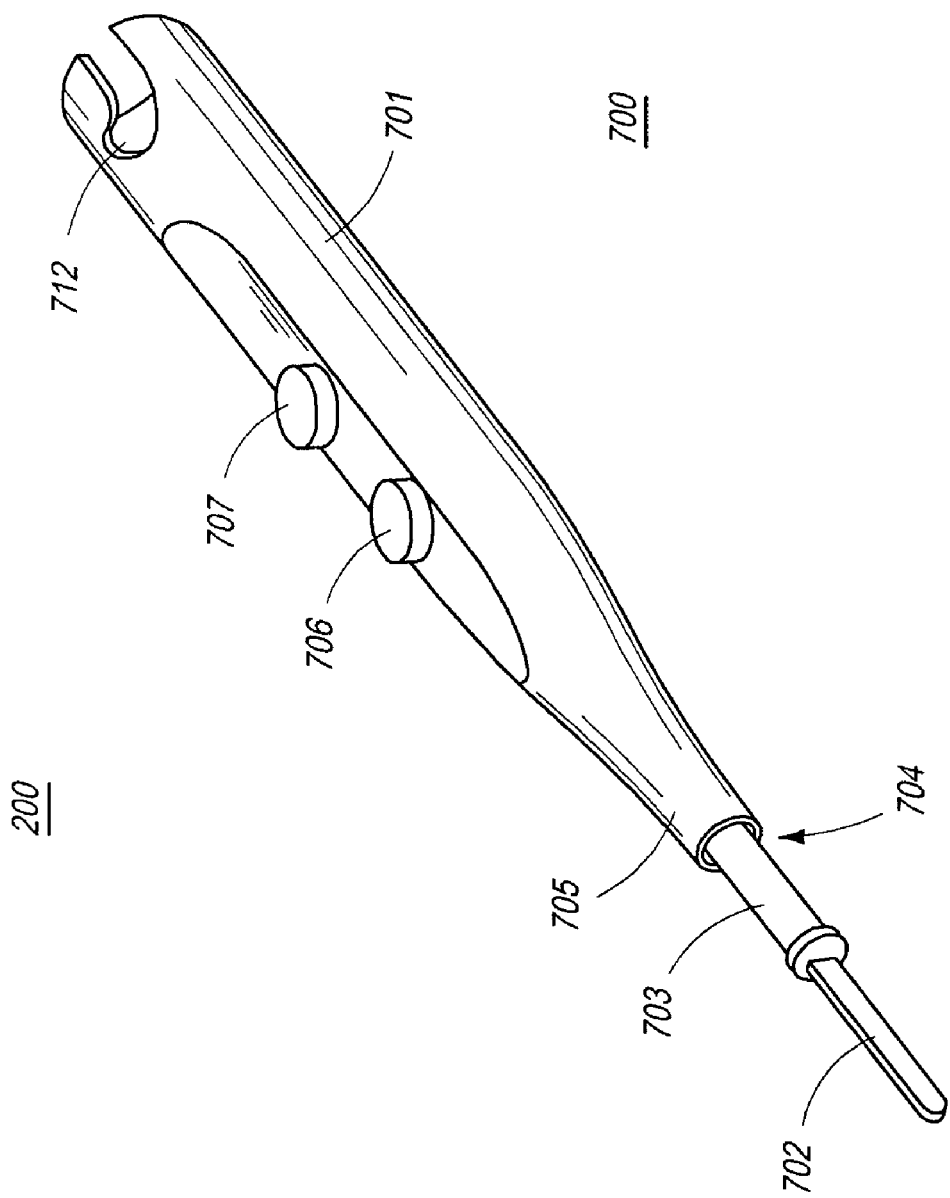
FIG. 19 is a perspective view drawing of the Housing of the Pencil shown in FIG. 18, with activation buttons and active electrode attached.

Referring to FIG. 19, the second embodiment in its completed configuration, but without Cap and Cable Assembly, is shown in perspective view. FIG. 19 shown Pencil 700 is comprised of a unitary Housing 701, active electrode 702 cutting blade, insulative plastic "over mold" electrode holder 703, which allows a user to safely remove active electrode 702 from Housing 701, and isolate heat generated by active electrode 702. Electrode holder 703, in turn, may be inserted into Housing front end aperture 704 at the corresponding "front" end 705 of Housing 701, which aperture 704 is formed to snugly receive electrode holder 703. Active electrode 702 generally extends through electrode holder 703, and into Housing 701, to reach crimped tubular end of Switch metal frame extending from the "front" of the Switch Cabinet (not shown in FIG. 19), once electrode holder 703 is inserted into aperture 704. Active electrode 702 may be finally positioned as shown in FIG. 19 during manufacture of Pencil 700, or thereafter by a user wishing to change active electrode blades. External activation Buttons 706 and 707 are shown, along with "j" slot 712 for locking Cap and Cable Assembly to Housing 701

Turning now to FIG. 20, Pencil 700 unitary Housing 701 is being joined with Cabinet 730. Housing openings 710 and 711 for Button stems (not shown) may also be seen, along with front end aperture 704. The simplicity of these components allow each piece to be independently grasped by automated machinery, oriented correctly for assembly, joined to one another, and pressed into place. All remaining components are similarly simple, easy and inexpensive to manufacture, and subject to fully automated assembly. Accordingly, from the view of Pencil 700 depicted in FIGS. 19 and 20, each piece of Pencil 700 may be, in order, joined to Housing 701, and pressed into place.

Figure 21:
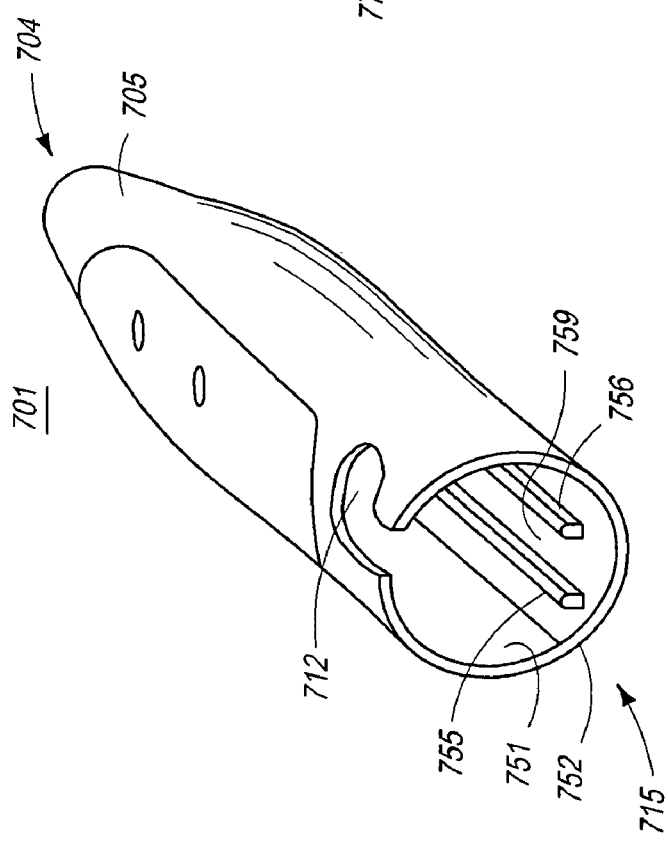
FIG. 21 is a perspective view drawing of the Housing shown in FIG. 19, viewed from a rear quarter of the Housing, in which a portion of the interior of the Housing, and some details of the Housing-to-Cap closure may be seen.

Turning to FIG. 21, the back end of Housing 701 is shown, with back end aperture 715, into which Switch Cabinet (not shown) may be placed, apparent. Lip 752 of back end aperture 715 appears in detail, with "j" slot 712 of Housing 701 ready for engagement with open end of Cap (not shown) for closure of Housing 701. Interior walls 751 of Housing 201, toward back end aperture 715, are differentially widened in this embodiment, to allow easy, fully automated, insertion of Cabinet (not shown) within Housing 701 during assembly. In addition, ramps 755 and 756, formed within interior of Housing 701, beginning at or nearer back end aperture 715, are formed on bottom interior surfaces 759 of Housing 701. Ramps 755 and 756 are generally lower in aspect near back end aperture 715, and they increase in height or depth as they approach front end 705 of Housing 701. Accordingly, the Switch Cabinet may be inserted into back end aperture 715 of Housing 701, and slid into Housing 701, the interior of which may narrow toward front end 705 of Housing 701, while ramps 755 and 756 within interior section 751 close around the Cabinet snugly, to keep it firmly positioned within Housing 701. At the end of its travel within Housing 701, the Cabinet may bear against Housing stop (not shown in FIG.

21), and crimped tubular end 535 of extension of Switch metal first frame 510 may reside snugly within, Housing 701 front end aperture 704.

Figure 22:
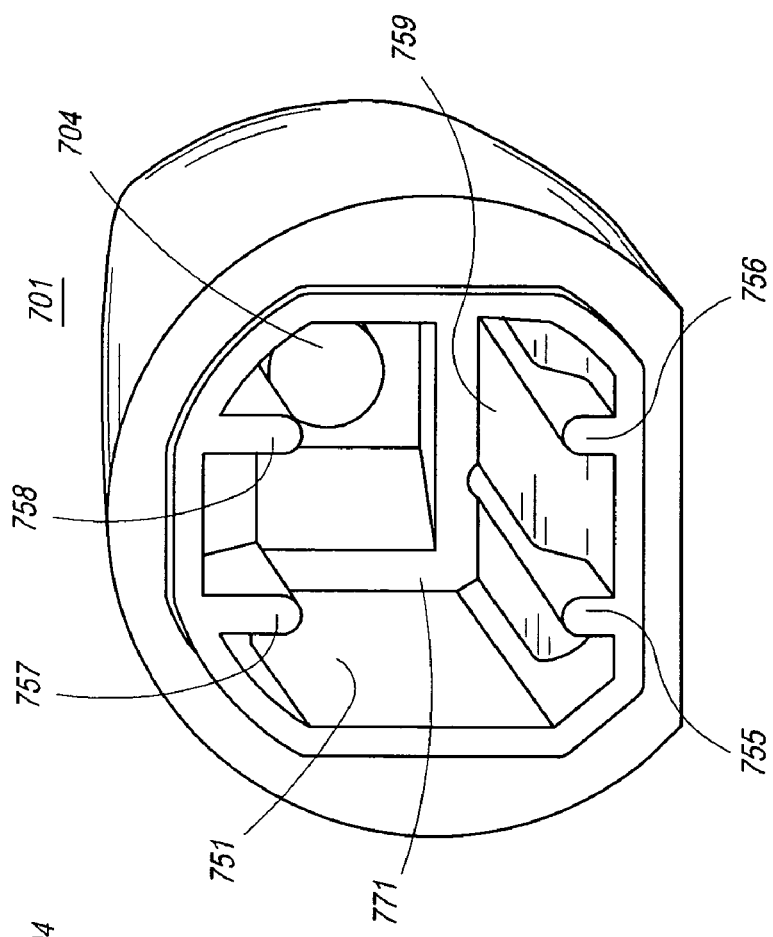
FIG. 22 is a foreshortened perspective view of a portion of the interior of the Housing of shown in FIG. 19, viewed from a rear quarter of the Housing, in which a view of the details at the front end interior of the Housing may be seen.

A foreshortened view of the front end interior of Housing 701 is shown in FIG. 22. Foreshortening this view of this section of the interior of Housing 701 allows us to see details at the front end interior of Housing 701. In FIG. 22, we can see a portion of interior walls 751 of Housing 701, near stop 771, is formed to receive the Cabinet. As the interior of this section of Housing 701 is just larger than the Cabinet, this section of Housing 701 may firmly hold the Cabinet within Housing 701, without material gap between the Cabinet and Housing 701 interior, which gap might allow vibration, or "play," between these components. The Cabinet may be formed with small protrusions (not shown) which may bear against one or more of the interior walls 751 of Housing 701 once the Cabinet is inserted into Housing 701. Such protrusions may be deformed as the Cabinet is pressed into position against stop 771, and held firmly within Housing 701 by the narrowness of interior walls 751 and one or more of the heightened ends of ramps 755 and 756 near stop 771. In the alternative, protrusions (not shown) may be formed on one or more interior surfaces of Housing 701, and a standard Cabinet (i.e., without protrusions) used. The protrusions, whether formed on the Cabinet or on the interior walls 751 of Housing 701, provide a "compression fit" of Switch Cabinet within Housing 701 after the Cabinet is pressed into final position within Housing 701, and against stop 771, during assembly. At the end of its travel within Housing 701, crimped tubular end 535 of extension 512 of Switch metal first frame resides snugly within Housing 701 front end aperture 704.

In FIG. 22, the front end interior of Housing 701 is formed with a "stop" 771 or "seat," up against which the Cabinet is pressed during assembly, and against which the Cabinet is seated after Cap (not shown in FIG. 22) is fitted over back end aperture 715 of Housing 701 to close Housing 701 over the Cabinet. Stop 771 is generally formed within Housing 701 to allow the Cabinet to slide forward in Housing 701 during assembly, sufficiently far to allow crimped tubular end 535 of Switch metal first frame 512 to extend into front end aperture 704 of Housing 701. The Cabinet, within which the Pencil Switch resides, and stop 771, are each formed to closely engage one another, and the Cabinet edges and stop 771 corners may each be rounded by adding a radius, or increasing the existing radius, to reduce strain and insure proper seating of the Cabinet against stop 771 within Housing 701.

Figure 23:
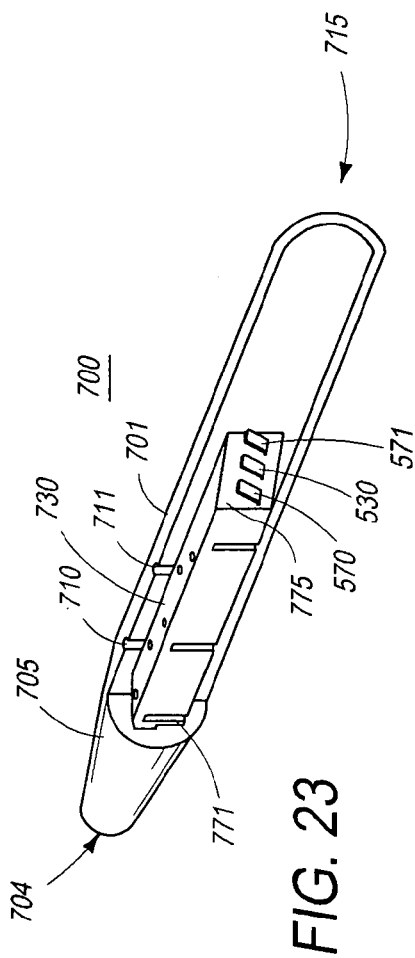
FIG. 23 is a rear quarter perspective cut away view drawing of the Pencil shown in FIG. 18, in which the second embodiment of the Switch of the present invention may be seen fully inserted into the Housing, and pushed up against the stop within the Housing.

Continuing with the assembly process, FIG. 23 shows Pencil 700 partially assembled in rear quarter perspective cut away view. In FIG. 23, Switch Cabinet 730 has been fully inserted into Housing 701, so that the forward end of Cabinet 730 bears against stop 771 within the interior of the forward end of Housing 701. In this position, Cabinet 730 determines the positions of crimped tubular end and extension of Switch metal frame (neither component shown here) firmly and snugly inserted into, and held within, the back portion of front end aperture 704. Cabinet 730 is retained in this position by front end 801 of Cap 720 (shown in FIGS. 24 and 25), with its tapered end 802, which is in length long enough to extend from the back-end of Cap 720 to the back end of Cabinet 730 once Cabinet 730 is positioned against stop 771 in Housing 701. Housing openings 710 and 711 may also be seen in FIG. 23, along with Housing 700 back end aperture 715. After Switch Cabinet 730 has been fully inserted into Housing 701, first insulation displacement connector 530 of Cabinet Top 590 (shown in FIG. 16), and second and third insulation displacement connectors 570 and 571 of Cabinet Bottom 600 (shown in FIG. 17) may each be seen. First insulation displacement connector 530, second insulation displacement connector 570, and third insulation displacement connector and 571, are each bent or twisted so as to receive and maintain contact with electrically conductive pins positioned within front end of Cap 720 (shown in FIG. 24).

Figure 24:
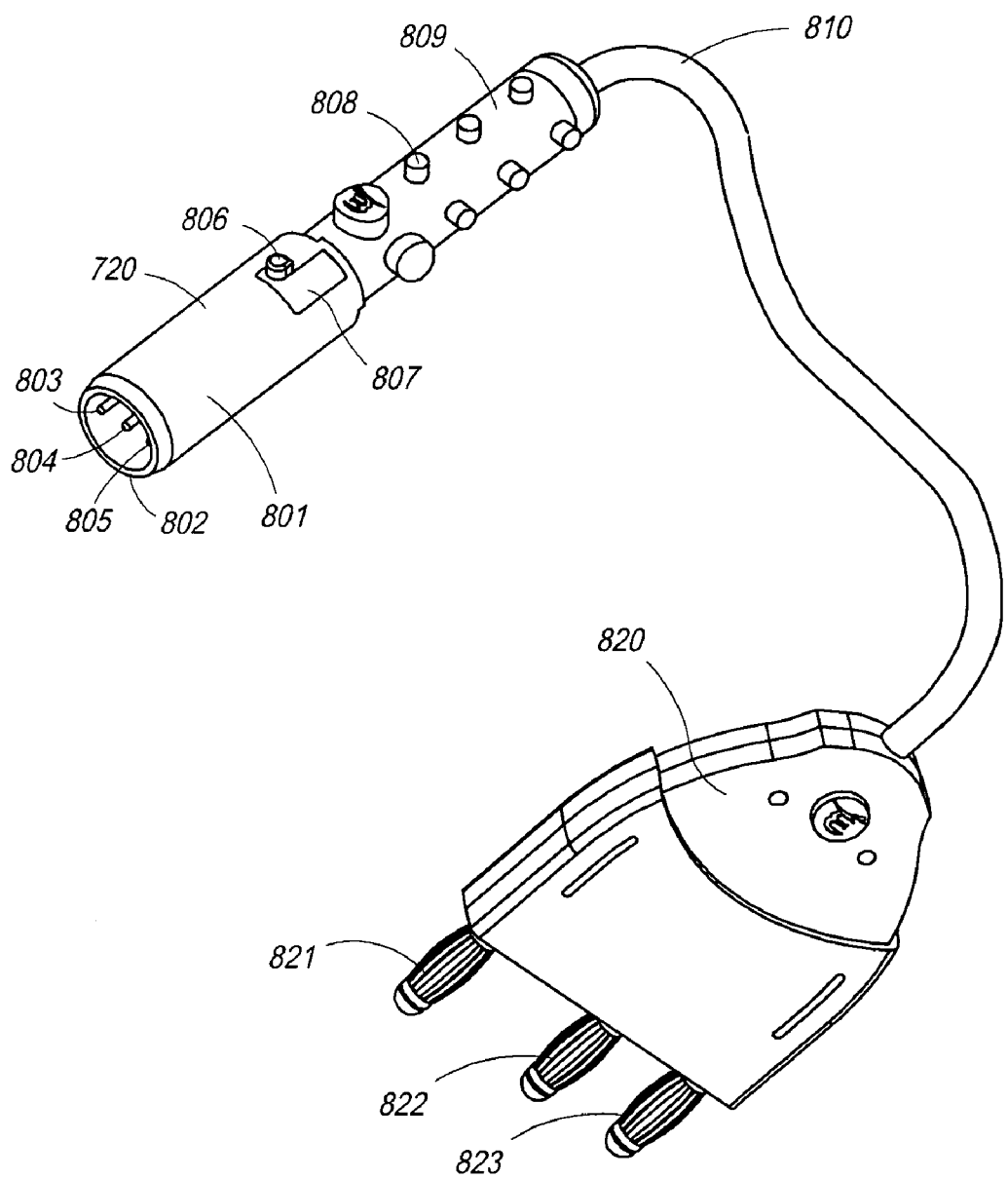
FIG. 24 is a perspective view of the Cap and Cable Assembly of the Pencil shown in FIG. 18, prior to final Cap overmolding, a portion of which Assembly may be joined to the Housing of FIG. 19 by insertion into the back end aperture of the Housing.

Closure Cap 720 is shown in FIG. 24, with some of its interior and exterior features, along with cable 810, and plug 820. Beginning at the front end 801 of Cap 720, is formed with Cap tapered end 802, which matches positionally, and coacts with, corresponding Housing 700 back end aperture 715. Electrically conductive pins 803, 804, and 805 are positioned within front end 801 of Cap 720, and extend into the plastic of front end 801 sufficiently far to anchor them in Cap 720. Cable 810, which may be of indeterminate length, connects electrically to pins 803, 804, and 805 within front end 801 of Cap 720, and provides electrical from to pins 803, 804, and 805 to, and through, plug 820, to plug pins 821, 822, and 823, at their back ends within plug 820.

Closure Cap 720 is formed to coact with Housing back end aperture 715 by insertion into back end aperture 715, so that electrically conductive pins 803, 804, and 805 are pressed up against first, second, and third insulation displacement connectors 530, 570, and 571, each of which resiliently bear against pins 803, 804, and 805 so long as Cap 720 remained fully inserted within Housing back end aperture 715. Cap 720 may also then be twisted within back end aperture 715, to lock Cap 720 and Housing 701 together, without losing contact between pins 803, 804, and 805 and first, second, and third insulation displacement connectors 530, 570, and 571. The locking action between Housing 701 and Cap 720 is accomplished by coaction of locking pin 806 with "j" slot 712 as front end 801 of Cap 720, with its tapered end 802, is twisted within Housing 700 after insertion into back end aperture 715. At the same time, locking indicator 807 moves into position, by the same twisting motion, so that it may show through "j" slot 712, so that the operator knows Cap 720 (and therefore the entire Cap and Cable assembly shown in FIG. 24) is securely affixed within Housing 701. Locking indicator 807 is preferably formed by creating the main body of Cap 720, in a green "first shot" of plastic, while the remainder of Cap 720 as it appears in FIG. 24 will be covered by a blue or gray second shot (over mold) of plastic. The final step in creating Cap 720 is a third shot (over mold) of plastic, of any color over back end 809 of Cap 720, to create a surface which is smooth to the touch, and easy to grip. Such third plastic shot will best be anchored to back end 809 of Cap 720, generally by anchor pins 808, which are covered by, and extend into the third plastic shot. With this construction, the small "window" of locking indicator 807 remains green, and will be visible after second shot mold is complete, but the window will only be visible when connector is inserted into the Housing of the pencil, and rotated correctly to the "lock" position.

Figure 25:
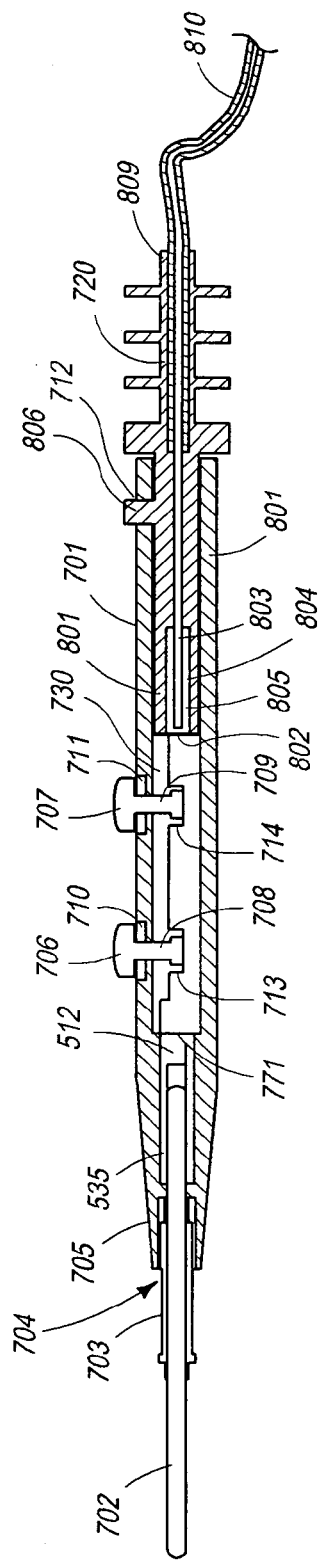
FIG. 25 is a cross section view drawing of the Pencil shown in FIG. 18, in which the second embodiment of the Switch of the present invention may be seen fully inserted into the Housing, and seated against the stop within the Housing, with the opening of the Cap portion of the Cap and Cable Assembly of shown in FIG. 24 fully engaged in the back aperture of the Housing of FIG. 19.

Continuing with the assembly process, FIG. 25 shows Pencil 700 fully assembled in cross section. In FIG. 25, Switch Cabinet 730 has again been fully inserted into Housing 701, so that the forward end of Cabinet 730 bears against stop 771 within forward end of Housing 701. Crimped tubular end 535 and extension of Switch metal first frame 512 are each shown here firmly and snugly inserted into the back portion of front end aperture 704, and held within aperture 704 by Cabinet 730, which is in turn retained in position by Cap 720 with front end 801, with its tapered end 802. Again, front end 801 and tapered end 802 of Cap 720 are in length long enough to extend within back end aperture 715 of Housing 701 to reach the back end of Cabinet 730 once the Cabinet is positioned against stop 771 in Housing 701. Housing openings 720 and 721 may also be seen in FIG. 25, into which stems 708 and 709 of Buttons 706 and 707 have been inserted. Stems 708 and 709 also extend through activation openings activation openings 713 and 714 in the top of Cabinet 730. Active electrode 702 may be seen in FIG. 25 inserted into, and extending through, electrode holder 703, within front end aperture 704 at front end 705 of Housing 701. In this embodiment, electrode holder 703 is a non-conductive, and insulative, plastic "over mold" extender used to hold active electrode 702, and connect it electrically to the crimped tubular end 535 and extension of Switch metal first frame 512. Generator conductors 810 may be seen, attached to Cap 720 at their point of insertion into back end 809 of Cap 720, and Cap 720 has been fitted into back end aperture 715 of Housing 701 to close Housing 701 over Cabinet 730. FIG. 25 also shows locking pin 806 within "j" slot 712, as front end 801 of Cap 720, with its tapered end 802, has been properly inserted into, and twisted within Housing 700 after insertion into back end aperture 715, to thereby lock Cap 720 and Housing 701 together. In such position, electrically conductive pins 803, 804, and 805 are pressed up against first, second, and third insulation displacement connectors 530, 570, and 571 (not shown in FIG. 25) of Cabinet 730, making and maintaining electrical contact between Generator conductors 810 and Cabinet 730 (and ultimately generator Other embodiments will be apparent to those skilled in the art from consideration of the specification and practice of the invention disclosed herein. It is intended that the specification and examples be considered as exemplary only, with a true scope of the invention being indicated by the following claims and equivalents.

What is claimed is:

1. A switch for an electrosurgical pencil comprising:
a first electrical circuit frame, formed of electrically conductive metal sufficiently thick to carry current sufficient to cut, coagulate, ablate, excise, cauterize, and seal tissues by application of electric current to biological tissue,
the first circuit frame having a first conducting strip, a first activation strap cut into the first conducting strip, a second activation strap cut into the first conducting strip, a first insulation displacement connector, and means for holding an active electrode,
the first activation strap having a first center landing, and a plurality of crimps along its length,
the first circuit frame having a plurality of first frame isthmus joined to the first conducting strip,
the first circuit frame having a first exterior portion joined to the plurality of first frame isthmus,
a second electrical circuit frame, formed of electrically conductive metal sufficiently thick to carry current sufficient to cut, coagulate, ablate, excise, cauterize, and seal tissues by application of electric current to biological tissue,
the second circuit frame having a second conducting strip, with a first dome contact and a second insulation displacement connector formed therein, and a third conducting strip, with a second dome contact and a third insulation displacement connector formed therein,
the second circuit frame having a plurality of second frame isthmus joined to the second conducting strip, and a plurality of third frame isthmus joined to the third conducting strip,
the second circuit frame having a second exterior portion joined to the plurality of second frame isthmus, and to the plurality of third frame isthmus,
a non-conductive base, molded in part over the first conducting strip, with first insulation displacement connector and means for holding an active electrode extending therefrom, the base formed with a first well, which exposes first activation strap, and a second well, which exposes second activation strap, and activation openings, through which appropriate means may be inserted to apply pressure to first and second activation straps from the exterior of the base,
a non-conductive top, molded in part over the second and third conducting strips, with second and third insulation displacement connectors extending therefrom, the top formed with a third well which exposes the first dome contact of the second conducting strip, and a fourth well, which exposes the second dome contact of the third conducting strip,
means for aligning and attaching the base to the top, so that the first activation strap of the first conducting strip may make electrical contact with the first dome contact of the second conducting strip when pressure is exerted against the first activation strap from the exterior of the switch, and the second activation strap of the second conducting strip may make electrical contact with the second dome contact of the third conducting strip when pressure is exerted against the second activation strap from the exterior of the switch,
whereby the first conducting strip and the second conducting strip may be temporarily electrically joined to allow a first current to flow therebetween, and the first conducting strip and the third conducting strip may be temporarily electrically joined to allow a second current to flow therebetween.

2. An electrosurgical pencil, into which the switch of claim 1 may be placed, comprising:
a generally cylindrical housing, into which a switch may be inserted, with a front end aperture, from which a portion of the switch may extend, and a back end aperture, into which the switch may be placed, the back end aperture having a lip,
the housing having an exterior, and an interior with interior walls, the interior walls being differentially widened toward the lip of the back end aperture,
the housing being formed to receive the switch snugly, the housing having a stop within, against which the switch may bear when it is inserted into the housing,
a switch formed according to claim 1, which may be inserted into the housing before the housing is closed,
a generally cylindrical closure cap, with an opening from which a cap push pin may extend, the opening having a lip,
the cap push pin formed within the closure cap so as to extend into the housing when the cap is positioned over the back end aperture of the housing, whereby the cap push pin may be used to push the switch into position against the stop during assembly, and hold the switch against the stop when the housing and the cap are joined.

3. An electrosurgical pencil, into which the switch of claim 1 may be placed, comprising:
a generally cylindrical housing, into which a switch may be inserted, with a front end aperture, from which a portion of the switch may extend, and a back end aperture, into which the switch may be placed, the back end aperture having a lip, the lip having a curved slot for receiving a locking pin,
the housing having an exterior, and an interior with interior walls, the interior walls being differentially widened toward the lip of the back end aperture, the housing being formed to receive the switch snugly, the housing having a stop within, against which the switch may bear when it is inserted into the housing, a switch formed according to claim 1, which may be inserted into the housing before the housing is closed, a generally cylindrical closure cap, with an opening from which electrical connectors may extend, the opening having a lip, the closure cap having a plurality of electrically conductive pins within the cap opening, the closure cap having generator conductors extending therethrough, the generator conductors having a plug attached thereto, and the closure cap having on its exterior a locking pin formed to fit within the curved slot of the housing when the closure cap is inserted into the back end aperture of the housing, and lock the closure cap to the housing when the cap is rotated within the back end aperture of the housing, whereby the switch is pressed into place against the stop, and the conductive pins are positioned against the insulation displacement connectors, and the cap is locked to the housing to close the pencil, when the cap is joined with the housing and rotated to lock the cap and housing together.

4. A series of multiple switch components for electrosurgical pencils comprising:

a metal sheet forming a first reel of indeterminate length, formed of electrically conductive metal sufficiently thick to carry current sufficient to cut, coagulate, ablate, excise, cauterize, and seal tissues by application of electric current to biological tissue, the first reel being cut to form a series of first electrical circuit frames, the frames each having a first conducting strip, a first activation strap cut into the first conducting strip, a second activation strap cut into the first conducting strip, a first insulation displacement connector, and means for holding an active electrode, the first activation straps each having a first center landing, and a plurality of crimps along their lengths, the first circuit frames each having a plurality of first frame isthmus joined to the first conducting strips, the first circuit frames each having a first exterior portion joined to the plurality of first frame isthmus, a metal sheet forming a second reel of indeterminate length, formed of electrically conductive metal sufficiently thick to carry current sufficient to cut, coagulate, ablate, excise, cauterize, and seal tissues by application of electric current to biological tissue, the second reel being cut to form a series of a second electrical circuit frames, the second circuit frames each having a second conducting strip, with a first dome contact and a second insulation displacement connector formed therein, and a third conducting strip, with a second dome contact and a third insulation displacement connector formed therein, the second circuit frames each having a plurality of second frame isthmus joined to the second conducting strips, and a plurality of third frame isthmus joined to the third conducting strips, the second circuit frames each having a second exterior portion joined to the plurality of second frame isthmus, and to the plurality of third frame isthmus, whereby the first circuit frames may be physically and electrically separated from one another by cutting the first between first frames, and the second circuit frames may be physically and electrically separated from one another by cutting the second reel between second frames, the first frames and second frames each overpoured into a first non-conductive material to surround the first frames in part, and surround the second frames in part, and the first frames and second frames positioned to allow electrical contact between the first frames and the second frames when the non-conductive material part surrounding the first frames is affixed to the non-conductive material part surrounding the second frames.

5. A method for assembling switches for electrosurgical pencils comprising:

forming a first array of first metal frames from a first metal reel of indeterminate length by stamping or cutting, crimping the first metal frames of the first array of metal frames to form insulation displacement connectors and tubular ends for receiving active electrodes, positioning the array of first metal frames in a first array mold of indeterminate length, the first array mold shaped to create an array of molded bottoms, forming a first array of first switch parts within the first array of molded bases by injecting non-conductive material into the first array mold, forming a second array of second metal frames from a second metal reel of indeterminate length by stamping or cutting, crimping the second metal frames of the second array of metal frames to form insulation displacement connectors, positioning the second array of second metal frames in a second array mold of indeterminate length, the second array mold shaped to create an array of molded tops, forming a second array of second switch parts within the second array of molded bases by injecting non-conductive material into the second array mold, positioning the first array of first switch parts adjacent the second array of second switch parts, and joining the first array of first switch parts to the second array of second switch parts so as to allow electrical connection between first switch parts and second switch parts, and separating each joined first and second switch parts from each adjacent joined first and second switch parts, whereby the first conducting strip and the second conducting strip may be temporarily electrically joined to allow a first current to flow therebetween, and the first conducting strip and the third conducting strip may be temporarily electrically joined to allow a second current to flow therebetween.

* * * * *